United States Patent
Whalley et al.

(10) Patent No.: US 11,318,109 B2
(45) Date of Patent: *May 3, 2022

(54) PHARMACEUTICAL COMPOSITION COMPRISING THE PHYTOCANNABINOIDS CANNABIDIVARIN (CBDV) AND CANNABIDIOL (CBD)

(71) Applicants: GW Pharma Limited, Cambridge (GB); Otsuka Pharmaceutical Co., Limited, Tokyo (JP)

(72) Inventors: Benjamin Whalley, Cambridge (GB); Claire Williams, Cambridge (GB); Gary Stephens, Cambridge (GB); Thomas Hill, Cambridge (GB)

(73) Assignees: GW Pharma Limited, Cambridge (GB); Otsuka Pharmaceutical Co., Limited, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/709,401

(22) Filed: Dec. 10, 2019

(65) Prior Publication Data

US 2020/0108027 A1 Apr. 9, 2020

Related U.S. Application Data

(63) Continuation of application No. 14/345,968, filed as application No. PCT/GB2012/052284 on Sep. 14, 2012, now Pat. No. 10,729,665.

(30) Foreign Application Priority Data

Sep. 29, 2011 (GB) .................................... 1116789

(51) Int. Cl.
| | |
|---|---|
| A61K 31/05 | (2006.01) |
| A61K 36/185 | (2006.01) |
| A61K 31/352 | (2006.01) |
| A61K 31/045 | (2006.01) |
| A61K 31/353 | (2006.01) |
| A61K 45/06 | (2006.01) |

(52) U.S. Cl.
CPC ............ *A61K 31/05* (2013.01); *A61K 31/045* (2013.01); *A61K 31/352* (2013.01); *A61K 31/353* (2013.01); *A61K 36/185* (2013.01); *A61K 45/06* (2013.01)

(58) Field of Classification Search
CPC ..................................................... A61K 31/05
See application file for complete search history.

(56) References Cited

U.S. PATENT DOCUMENTS

| | | |
|---|---|---|
| 6,403,126 B1 | 6/2002 | Webster |
| 6,949,582 B1 | 9/2005 | Wallace |
| 8,293,786 B2 | 10/2012 | Stinchcomb |
| 8,673,368 B2 | 3/2014 | Guy et al. |
| 9,017,737 B2 | 4/2015 | Kikuchi et al. |
| 9,023,322 B2 | 5/2015 | Van Damme et al. |
| 9,066,920 B2 | 6/2015 | Whalley et al. |
| 9,095,554 B2 | 8/2015 | Lewis et al. |
| 9,125,859 B2 | 9/2015 | Whalley et al. |
| 9,168,278 B2 | 10/2015 | Guy et al. |
| 9,259,449 B2 | 2/2016 | Raderman |
| 9,474,726 B2 | 10/2016 | Guy et al. |
| 9,522,123 B2 | 12/2016 | Whalley et al. |
| 9,730,911 B2 | 8/2017 | Verzura et al. |
| 9,956,183 B2 | 5/2018 | Guy et al. |
| 9,956,184 B2 | 5/2018 | Guy et al. |
| 9,956,185 B2 | 5/2018 | Guy et al. |
| 9,956,186 B2 | 5/2018 | Guy et al. |
| 10,729,665 B2 * | 8/2020 | Whalley .............. A61K 31/045 |
| 2004/0049059 A1 | 3/2004 | Mueller |
| 2004/0110828 A1 | 6/2004 | Chowdhury et al. |

(Continued)

FOREIGN PATENT DOCUMENTS

| | | |
|---|---|---|
| CA | 2737447 | 10/2012 |
| CA | 2859934 | 3/2016 |

(Continued)

OTHER PUBLICATIONS

[No Author Listed] "Cannabidiol Therapy for Aicardi Syndrome" Aug. 2014, 4 pages.

(Continued)

*Primary Examiner* — Rei Tsang Shiao
(74) *Attorney, Agent, or Firm* — Morrison & Foerster LLP

(57) ABSTRACT

This invention relates to a pharmaceutical composition comprising or consisting essentially of the phytocannabinoids cannabidivarin (CBDV) and cannabidiol (CBD). The composition is particularly safe and efficacious for use in the treatment of neurological conditions, characterized by hyper-excitability of the central nervous system, convulsions or seizures such as occur in epilepsy. Preferably the CBDV and the CBD are present with at least one non-cannabinoid component of *cannabis* such as one or more terpenes or a terpene fraction. More particularly the composition further comprises one or more cannabichromene type compounds. Particularly cannabichromene propyl variant (CBCV) and/or cannabichromene (CBC). More particularly still the composition is absent or substantially absent of other cannabinoids, including in particular tetrahydrocannabinol (THC) and tetrahydrocannabivarin (THCV), which would normally be present in significant amounts in *cannabis* chemotypes bred to contain a significant amount of CBDV and/or CBD.

42 Claims, 5 Drawing Sheets

(56) References Cited

U.S. PATENT DOCUMENTS

| | | |
|---|---|---|
| 2005/0042172 A1 | 2/2005 | Whittle |
| 2005/0266108 A1 | 12/2005 | Flockhart et al. |
| 2006/0039959 A1 | 2/2006 | Wessling |
| 2007/0060638 A1 | 3/2007 | Olmstead |
| 2008/0119544 A1 | 5/2008 | Guy et al. |
| 2008/0188461 A1 | 8/2008 | Guan |
| 2009/0264063 A1 | 10/2009 | Tinsley et al. |
| 2009/0306221 A1 | 12/2009 | Guy et al. |
| 2010/0239693 A1 | 9/2010 | Guy et al. |
| 2010/0317729 A1 | 12/2010 | Guy et al. |
| 2011/0028431 A1 | 2/2011 | Zerbe et al. |
| 2011/0038958 A1 | 2/2011 | Kikuchi et al. |
| 2011/0082195 A1 | 4/2011 | Guy et al. |
| 2012/0004251 A1 | 1/2012 | Whalley et al. |
| 2012/0165402 A1 | 6/2012 | Whalley et al. |
| 2012/0183606 A1 | 7/2012 | Bender et al. |
| 2012/0202891 A1 | 8/2012 | Stinchcomb et al. |
| 2012/0270845 A1 | 10/2012 | Bannister et al. |
| 2013/0209483 A1 | 8/2013 | McAllister |
| 2013/0245110 A1 | 9/2013 | Guy et al. |
| 2013/0296398 A1 | 11/2013 | Whalley et al. |
| 2014/0100269 A1 | 4/2014 | Goskonda et al. |
| 2014/0155456 A9 | 6/2014 | Whalley et al. |
| 2014/0243405 A1 | 8/2014 | Whalley et al. |
| 2014/0335208 A1 | 11/2014 | Cawthorne et al. |
| 2014/0343044 A1 | 11/2014 | Ceulemens |
| 2015/0111939 A1 | 4/2015 | Gruening et al. |
| 2015/0181924 A1 | 7/2015 | Llamas |
| 2015/0320698 A1 | 11/2015 | Whalley et al. |
| 2015/0343071 A1 | 12/2015 | Vangara |
| 2015/0359756 A1 | 12/2015 | Guy et al. |
| 2016/0166498 A1 | 6/2016 | Anastassov |
| 2016/0166514 A1 | 6/2016 | Guy et al. |
| 2016/0166515 A1 | 6/2016 | Guy et al. |
| 2016/0220529 A1 | 8/2016 | Guy et al. |
| 2016/0256411 A1 | 9/2016 | Aung-Din |
| 2017/0007551 A1 | 1/2017 | Guy et al. |
| 2017/0172939 A1 | 6/2017 | Guy et al. |
| 2017/0172940 A1 | 6/2017 | Guy et al. |
| 2017/0172941 A1 | 6/2017 | Guy et al. |
| 2017/0173043 A1 | 6/2017 | Guy et al. |
| 2017/0173044 A1 | 6/2017 | Guy et al. |
| 2017/0181982 A1 | 6/2017 | Guy et al. |
| 2017/0231923 A1 | 8/2017 | Guy et al. |
| 2017/0239193 A1 | 8/2017 | Guy et al. |
| 2017/0246121 A1 | 8/2017 | Guy et al. |
| 2017/0266126 A1 | 9/2017 | Guy et al. |
| 2017/0273913 A1 | 9/2017 | Whalley et al. |
| 2018/0071210 A1 | 3/2018 | Wilkhu et al. |
| 2018/0228751 A1 | 8/2018 | Stott et al. |
| 2018/0338931 A1 | 11/2018 | Guy et al. |
| 2019/0167583 A1 | 6/2019 | Shah et al. |
| 2019/0175547 A1 | 6/2019 | Stott et al. |

FOREIGN PATENT DOCUMENTS

| | | |
|---|---|---|
| CN | 101040855 | 9/2007 |
| CN | 103110582 | 5/2013 |
| DE | 102012-105063 | 12/2013 |
| EP | 2448637 | 5/2012 |
| GB | 2384707 | 8/2003 |
| GB | 2434097 | 7/2007 |
| GB | 2434312 | 7/2007 |
| GB | 2450753 | 1/2009 |
| GB | 0911580.9 | 7/2009 |
| GB | 2456183 | 7/2009 |
| GB | 2471523 | 1/2011 |
| GB | 2478595 | 9/2011 |
| GB | 2479153 | 10/2011 |
| GB | 2471565 | 7/2012 |
| GB | 2478072 | 12/2012 |
| GB | 2478074 | 12/2012 |
| GB | 2492487 | 1/2013 |
| GB | 2487712 | 10/2015 |
| GB | 2531282 | 4/2016 |
| GB | 2438682 | 12/2017 |
| WO | WO 2002/064109 | 8/2002 |
| WO | WO 2003/099302 | 12/2003 |
| WO | WO 2004/016246 | 2/2004 |
| WO | WO 2004/016277 | 2/2004 |
| WO | WO 2006/054057 | 5/2006 |
| WO | WO 2006/133941 | 12/2006 |
| WO | WO 2007/083098 | 7/2007 |
| WO | WO 2007/138322 | 12/2007 |
| WO | WO 2008/019146 | 2/2008 |
| WO | WO 2008/094181 | 8/2008 |
| WO | WO 2008/129258 | 10/2008 |
| WO | WO 2008/144475 | 11/2008 |
| WO | WO 2008/021394 | 12/2008 |
| WO | WO 2008/146006 | 12/2008 |
| WO | WO 2009/007697 | 1/2009 |
| WO | WO 2009/007698 | 1/2009 |
| WO | WO 2009/020666 | 12/2009 |
| WO | WO 2010/012506 | 2/2010 |
| WO | WO 2011/001169 | 1/2011 |
| WO | WO 2011/121351 | 10/2011 |
| WO | WO 2012/033478 | 3/2012 |
| WO | WO 2012/093255 | 7/2012 |
| WO | WO 2013/032351 | 3/2013 |
| WO | WO 2014/146699 | 9/2014 |
| WO | WO 2015/142501 | 9/2015 |
| WO | WO 2015/184127 | 12/2015 |
| WO | WO 2015/193667 | 12/2015 |
| WO | WO 2015/193668 | 12/2015 |
| WO | WO 2016/059405 | 4/2016 |
| WO | WO 2016/118391 | 7/2016 |
| WO | WO 2016/147186 | 9/2016 |
| WO | WO 2016/022936 | 11/2016 |
| WO | WO 2017/168138 | 10/2017 |

OTHER PUBLICATIONS

[No Author Listed], "Missouri House passes cannabis extract legislation," Kansas City Star, 2014, https://kansascity.com/news/politics-government/article346747.html, 2 pages.

[No Author Listed], Cover and Table of Contents, J Pharmacology and Exp Therapeutics, Feb. 2010, 332(2), 4 pages.

Alger, "Not Too Excited? Thank Your Endocannabinoids," Neuron., Aug. 2006, 51(4):393-395.

American Epilepsy Society, Three Studies Shed New Light on the Effectiveness of Cannabis in Epilepsy, Oct. 14, 2014, 2 pages.

Ames et al., "Anticonvulsant effect of cannabidiol," S. Afr Med. J., Jan. 1986, 69(1):14.

Arain et al., "Pregabalin in the Management of Partial Epilepsy," Neuropsychiatr Dis Treat., Aug. 2009, 5:407-413.

Arslan and Tirnaksiz, "Self-emulsifying Drug Delivery Systems," FABAD J Pharm Sci, 2013,38(1):55-64.

Arzimanoglou et al., "All children who experience epileptic falls do not necessarily have Lennox-Gastaut syndrome . . . but many do," Epileptic Discord, 2011, 13:S3-S13.

AU Re-examination report—standard patent for Australian Patent No. 2012204800, dated May 3, 2019, 7 pages.

AU Third Party Observations for Application No. AU2012314129, dated Mar. 19, 2015, 51 pages.

Australian Office Action in Application No. 2012204800, dated Oct. 22, 2019, 5 pages.

Avoli et al., "Cellular and molecular mechanisms of epilepsy in the human brain," Prog Neurobiol., 2005, 77(3):166-200.

Bakhsm, "Key Attributes of TKDL," Miftaah-al-Khazaain, 1930, 607-608 (with English translation).

Bancaud et al., "Proposal for Revised Clinical and Electroencephalographic Classification of Epileptic Seizures," Epilepsia, Aug. 1981, 22(4):489-501.

Banerjee et al., "Case Report: Aicardi syndrome: A report of five Indian cases," Neurology India, Mar. 2006, 54(1): 91-93.

Barker-Haliski et al, "How Clinical Development Can, and Should. Inform Translational Science," Neuron, Nov. 2014, 84: 582-593.

Benowitz and Jones, "Cardiovascular and metabolic considerations in prolonged cannabinoid administration in man," J Clin Pharm, 1981, 21: 214S-223S.

(56) References Cited

OTHER PUBLICATIONS

Benowitz et al., "Metabolic and Psychophysiologic studies of cannabidiol hexobarbital interaction," Clin Pharmacol Ther., 1980, 28(1):115-120.

Bertram, "The Relevance of Kindling for Human Epilepsy," Epilepsia, Apr. 2007, 48(Suppl. 2):65-74.

Bhatt et al., "Indigenous Plants in Traditional Healthcare System in Kedarnath Valley of Western Himalaya," Indian J Tradit Knowl., Apr. 2008, 7(2):300-310.

Bhattacharyya et al., "Modulation of mediotemporal and ventrostriatal function in humans by Delta9-tetrahydrocannabinol: a neural basis for the effects of Cannabis sativa on learning and psychosis," Arch Gen Psychiatry., 2009, 66:442-451.

BipolarHealthGroup.org [online], "Charlotte's Web Hemp Remedy," Bipolar Health Group, available on or before Sep. 6, 2017, retrieved on May 21, 2018, URL <http:/bipolarhealthgroup.org/index.php/charlottes-web-hemp-remedy/>, 6 pages.

Booth et al., "Legalization's opening of medical pot research is dream and nightmare," Denver Post, Dec. 14, 2013, retrieved on Feb. 8, 2017, URL <https://www.denverpost.com/2013/12/14/legalizations-opening-of-medical-pot-research-is-dream-and-nightmare/>, 6 pages.

Bostanci et al., "The effects of octanol on penicillin induced epileptiform activity in rats: An in vivo study," Epilepsy Res., Jul. 27, 2006, 71(2-3):188-194.

Braida et al., "Post-ischemic treatment with cannabidiol prevents electroencephalographic flattening, hyper locomotion and neuronal injury in gerbils" Neuroscience Letters., 2003, 346:61-64.

Brodie et al., "Combining antiepileptic drugs—rational polytherapy?", Seizure, 2011, vol. 20, pp. 369-375.

Brust et al., "Marijuana use and the risk of new onset seizures," Trans Am Clin Climatol Assoc., 1992, 103:176-181.

Carlini et al., "Hypnotic and Antiepileptic Effects of Cannabidiol," J Clin Pharmacol., Aug.-Sep. 1981, 21(8-9 Suppl):417S-427S.

Castel-Branco et al., "The Maximal Electroshock Seizure (MES) Model in the Preclinical Assessment of Potential New Antiepileptic Drugs," Methods Find Exp Clin Pharmacol., 2009, 31(2); 101-106.

Charlotte's Web [online], "When to Expect Results from CW Hemp Oil", Mar. 13, 2017, retrieved on May 21, 2018, URL https://www.cwhemp.com/blog/expecting-results-from-hemp, 6 pages.

Charlotte's Web [online], "Whole-Plant Cannabinoids Outperform Single Molecule Compounds," CWHemp.com, Jan. 11, 2017, retrieved on Jun. 16, 2017, URL <https://www.cwhemp.com/blog/whole-plant-cw-hemp-cannabinoids>, 5 pages.

ChildNeurologyFoundation.org [online], "Disorder Directory: Learn from the Experts—LGS (Lennon-Gastaut Syndrome)," Child Neurology Foundation, available on or before Sep. 6, 2005, retrieved on May 21, 2018, URL http://www.childneurologyfoundation.org/disorders/lgs-lennon-gastaut-syndrome, 10 pages.

Chiron and Dulac, "The Pharmacologic Treatment of Dravet Syndrome," Epilepsia, 2011, 52(Suppl. 2): 72-75.

Chiu et al., "The Influence of Cannabidiol and Δ9-Tetrahydrocannabinol on Cobalt Epilepsy in Rats," Epilepsia., 1979, 20:365-375.

Conry et al., "Clobazam in the treatment of Lennox-Gastaut syndrome," Epilepsia, May 2009, 50(5):1158-1166.

Consroe and Sandyk, "Chapter 12: Potential Role of Cannabinoids for Therapy of Neurological Disorders," Marijuana / Cannabinoids: Neurobiology and Neurophysiology, ed. L. Murphy, 1992, 459-524.

Consroe et al., "Anticonvulsant drug antagonism of Δ9tetrahydrocannabinol-induced seizures in rabbits," Res Commun Chem Pathol Pharmacol., Jan. 1977, 16(1):1-13.

Consroe et al., "Anticonvulsant Interaction of Cannabidiol and Ethosuximide in Rats," J. Pharm. Pharmac., Aug. 1977, 29(8):500-501.

Consroe et al., "Anticonvulsant Nature of Marihuana Smoking," JAMA, Oct. 1975, 234(3):306-307.

Consroe et al., "Cannabidiol—Antiepileptic Drug Comparisons and Interactions in Experimentally Induced Seizures in Rats," J. Pharm. Exp. Therap., Apr. 1977, 201(1):26-32.

Consroe et al., "Controlled clinical trial of cannabidiol in Huntington's Disease," Pharmacology Biochemistry & Behavior, 1991, 40:701-708.

Consroe et al., "Effects of Cannabidiol on Behavioral Seizures Caused by Convulsant Drugs or Current in Mice," Eur J Pharm, Sep. 1982, 83(3-4):293-298.

Consroe et al., "Chapter 2: Therapeutic Potential of Cannabinoids in Neurological Disorders," Cannabinoids as Therapeutic Agents, R. Mechoulam ed., 1986, 21-49.

Cortesi et al., "Potential therapeutical effects of cannabidiol in children with pharmacoresistant epilepsy," Med Hypotheses., 2007, 68(4):920-921.

Cortez and Snead, "Chapter 10: Pharmacologic Models of Generalized Absence Seizures in Rodents," Models of Seizures and Epilepsy, 2006, 111-126.

Crespel, et al., "Chapter 14: Lennox-Gastaut Syndrome," Epileptic Syndromes in Infancy, Childhood, and Adolescence, 2012, 5th Edition, ed. M. Bureau, 189-216.

Cunha et al., "Chronic Administration of Cannabidiol to Healthy Volunteers and Epileptic Patients," Pharmacology, 1980. 21(3):175-185.

Curia et al., "The pilocarpine model of temporal lobe epilepsy," J Neuroscience Methods, Jul. 2008, 172(2-4): 143-157.

Czapinski et al., "Mar. 17, 2008: Randomized 36-month comparative study of valproic acid (VPA), phenytoin (PHT), phenobarbital (PB) and carbamazepine (CBZ) efficacy in patients with newly diagnosed epilepsy with partial complex seizures," J. Neurol. Sci., Sep. 1997, 150(1):S162-S163.

Dasa et al., "Key Attributes of TKDL: Ganja," Brhat Nighantu Ratnakara (Saligramanighantubhusanam), 1997, 6 pages (with English translation).

Davis and Ramsey, "Antiepileptic action of marihuana-active substances," Federation Proceedings., Mar. 1949, 8:284-285.

Davis et al., "A Predominant Role for Inhibition of the Adenylate Cyclase/Protein Kinase A Pathway in ERK Activation by Cannabinoid Receptor 1 in NIE-115 Neuroblastoma Cells," J Biol Chem., Dec. 2003, 278(49): 48973-48980.

De Meijer, "Chapter 5: The Chemical Phenotypes (Chemotypes) of Cannabis," Handbook of Cannabis, ed. Roger G. Pertwee, 2014, 89-110.

De Oliveira, et al., "Anticonvulsant activity of β-caryophyllene against pentylenetetrazol-induced seizures," Epilepsy Behav, Mar. 2016, 56:26-31.

Deshpande et al., "Cannabinoid CB1 Receptor Antagonists Cause Status Epilepticus-like Activity in the Hippocampal Neuronal Culture Model of Acquired Epilepsy," Neurosci Lett., Jan. 2007, 411: 11-16.

Devinsky et al., "Cannabidiol: Pharmacology and potential therapeutic role in epilepsy and other neuropsychiatric disorders," Epilepsia, 2014, 55(6):791-802.

Dravet, "The core Dravet syndrome phenotype," Epilepsia, Apr. 2011, 52(Suppl 2): 3-9.

Dreifus et al., "Proposal for Revised Clinical and Electroencephalographic Classification of Epileptic Seizures," Epilepsia, Aug. 1981, 22:489-501.

Dulac and Kaminska, "Use of Lamotrigine in Lennox-Gastaut and Related Epilepsy Syndromes," J. Child Neurolog., Nov. 1997, 12(S1): S23-S29.

Dulac et al., "Vigabatrin in Childhood Epilepsy," J. Child Neurolog., 1991, 6(S2): S30-S37.

Eadie, "Shortcomings in the current treatment of epilepsy," Expert Rev Neurother., Dec. 2012, 12(12): 1419-1427.

Eggers, "Temporal lobe epilepsy is a disease of faulty neuronal resonators rather than oscillators, and all seizures are provoked, usually by stress," Med Hypotheses, 2007, 69(6): 1284-1289.

Engel et al., "Chapter 1: What Should be Modeled?," In Models Seizure Epilepsy., 2006, 14 pages.

Engel, "Report of the ILAE Classification Core Group," Epilepsia, 2006, 47(9): 1558-1568.

EPO Annex to the Communication in Opposition for European Appln. No. 10734541.5, dated Jan. 28, 2016, 5 pages.

EPO Auxiliary Requests to the File in European Patent No. EP2448637, dated Nov. 2, 2016, 45 pages.

(56) References Cited

OTHER PUBLICATIONS

EPO Communication of a Notice of Opposition in European Appln. No. 10734541.5, dated Dec. 17, 2014, 1 page.
EPO Communication Pursuant to Article 94(3) EPC in European Appln. No. 10734541.5, dated Oct. 23, 2012, 3 pages.
EPO Interlocutory Decision in Opposition in European Appln. No. EP2448637, dated Dec. 15, 2016, 91 pages.
EPO Letter from Opponent Regarding Oral Proceedings in European Patent No. EP2448637, dated Oct. 20, 2016, 6 pages.
EPO Notice of Appeal in European Patent No. EP2448637, dated Feb. 14, 2017, 5 pages.
EPO Notice of Opposition to a European Patent No. EP2448637, Dated Dec. 5, 2014, 20 pages.
EPO Opponent Response to the Preliminary Opinion of the Opposition Division in European Patent No. EP2448637, dated Jun. 23, 2016, 27 pages.
EPO Opponent Response to the Preliminary Opinion of the Opposition Division in European Patent No. EP2448637, dated Sep. 9, 2016, 25 pages.
EPO Opponent Response to the Written Submissions in European Patent No. EP2448637, dated Oct. 12, 2016, 18 pages.
EPO Opponent Response to the Written Submissions in European Patent No. EP2448637, dated Oct. 20, 2016, 3 pages.
EPO Opponent Written Submission in European Patent No. EP2448637, dated Nov. 4, 2016, 3 pages.
EPO Opposition, Expert Statement of Dr. Emma Louise Cheetham in European Appln. No. EP10734541.5, dated Nov. 4, 2016, 1 pages.
EPO Opposition, Expert Statement of Professor Anthony G Marson in European Appln. No. EP10734541.5 , dated Jun. 14, 2016, 9 pages.
EPO Opposition, Expert Statement of Professor Benjamin J. Whalley in European Appln. No. EP10734541.5, dated Sep. 9, 2016, 11 pages.
EPO Opposition, Expert Statement of Vincenzo Di Marzo in European Appln. No. EP10734541.5, dated Sep. 9, 2016, 10 pages.
EPO Opposition, Supplemental Expert Statement of Professor Benjamin J. Whalley, dated Nov. 4, 2016, 9 pages.
EPO Reply of the Patent Proprietor to the Notice(s) of Opposition in European Patent No. 2448637, dated May 28, 2015, 12 pages.
EPO Reply to Examination Report in European Patent Application No. 10734541.5, dated Feb. 15, 2013, 54 pages.
EPO Reply to Opponent's Written Submission in European Patent No. EP2448637, dated Nov. 4, 2016, 13 pages.
EPO Reply to Opponent's Written Submissions in European Patent No. EP2448637, dated Oct. 18, 2016, 5 pages.
EPO Reply to Preliminary Opinion and Opponent's Observations in European Patent No. EP2448637, dated Sep. 9, 2016, 65 pages.
EPO Reply to Proprietor's Statement of Grounds of Appeal in European Patent No. EP2448637, dated Sep. 8, 2017, 5 pages.
EPO Response to the Statement of Grounds of Appeal in European Patent No. 2448637, dated Sep. 5, 2017, 17 pages.
EPO Statement of Grounds of Appeal in European Appln. No. 10734541.5 , dated Apr. 21, 2017, 14 pages.
EPO Statement of Grounds of Appeal in European Appln. No. 10734541.5, dated Apr. 12, 2017, 6 pages.
EPO Statement of Opposition in European Appln. No. EP10734541. 5, dated Dec. 5, 2014, 14 pages.
EPO Third Party Observations in European Appln. No. EP10734541. 5, dated Apr. 3, 2017, 19 pages.
EPO Third Party Observations in European Appln. No. EP11712658. 1, dated Nov. 22, 2013, 14 pages.
Fariello, "Parenteral Penicillin in Rats: An Experimental Model of Multifocal Epilepsy," Epilepsia, 1976, 17:217-222.
FDA [online], "Warning Letters and Test Results for Cannabidiol-Related Products," 2015 Warning Letters, retrieved on Nov. 14, 2017, URL <https://www.fda.gov/newsevents/publichealthfocus/ucm484109.htm>, 4 pages.
FDA [online], "Warning Letters and Test Results for Cannabidiol-Related Products," 2016 Warning Letters, retrieved on Nov. 14, 2017, URL <https://www.fda.gov/newsevents/publichealthfocus/ucm484109.htm>, 4 pages.
FDA, Guidance for Industry: Estimating the maximum Safe Starting Dose in Initial Clinical Trials for Therapeutics in Adult Healthy Volunteers, U.S. Dept of Health and Human Services: Food and Drug Administration, Jul. 2005, 30 pages.
Ferdinand et al., "Cannabis—Psychosis Pathway Independent of Other Types of Psychopathology," Schizophrenia Research, 2005, 79:289-295.
Fisher et al., "The impact of epilepsy from the patient's perspective I. Descriptions and subjective perceptions," Epilepsy Research, 2000, 41(1):39-51.
Friedman et al., "Cannabinoids in the Treatment of Epilepsy", New England Journal of Medicine, 2015, vol. 373, pp. 1048-1058.
Gabor et al., "Lorazepam Versus Phenobarbital: Candidates for Drug of Choice for Treatment of Status Epilepticus," J Epilepsy, Jan. 1990, 3(1):3-6.
Gallily et al., "Overcoming the Bell-Shaped Dose-Response of Cannabidiol by Using Cannabis Extract Enriched in Cannabidiol," Pharmacology & Pharmacy, Jan. 2015, 6:75-85.
Gardner [online], "Comes Now Epidiolex (FDA Approves IND Studies of CBD)," BeyondTHC.com, Oct. 22, 2013, retrieved on Jan. 31, 2018, URL <http://www.beyondthc.com/comes-now-epidiolex-fda-approves-ind-studies-of-cbd>, 4 pages.
Gastaut., "Clinical and Electroencephalographical Classification of Epileptic Seizures," Epilepsia, 1970, 11:102-113.
Gaston et al., "Interactions between cannabidiol and commonly used antiepileptic drugs" Epilepsia, 2017, vol. 58, No. 9, pp. 1586-1592.
GB Combined Search and Examination Report in GB Appln. No. GB1116789.7, dated Jan. 4, 2012, 8 pages.
GB Combined Search and Examination Report in Application No. GB1611544.6, dated Mar. 29, 2017, 8 pages.
GB Combined Search and Examination Report in GB Appln. No. GB1100043.7, dated Mar. 25, 2011, 8 pages.
GB Combined Search and Examination Report in GB Appln. No. GB1121919.3, dated Feb. 29, 2012, 8 pages.
GB Combined Search and Examination Report in GB Appln. No. GB1410771.8, dated Feb. 27, 2015, 7 pages.
GB Combined Search and Examination Report in GB Appln. No. GB1414813.4, dated Sep. 5, 2014, 8 pages.
GB Combined Search and Examination Report in GB Appln. No. GB1418166.3, dated Jul. 2, 2015, 8 pages.
GB Combined Search and Examination Report in GB Appln. No. GB1418170.5, dated Jul. 2, 2015, 6 pages.
GB Combined Search and Examination Report in GB Appln. No. GB1418171.3, dated Jun. 29, 2015, 8 pages.
GB Combined Search and Examination Report in GB Appln. No. GB1506550.1, dated Feb. 5, 2016, 9 pages.
GB Combined Search and Examination Report in GB Appln. No. GB1514079.1, dated May 4, 2016, 9 pages.
GB Combined Search and Examination Report in GB Appln. No. GB1605448.8, dated Jan. 12, 2017, 6 pages.
GB Combined Search and Examination Report in GB Appln. No. GB1621480.1, dated Sep. 22, 2017, pages.
GB Examination Report in GB Appln. No. GB1100043.7, dated Mar. 18, 2014, 2 pages.
Gedde [online], "Clinical Experience with Cannabis in Treatment-Resistant Pediatric Epilepsy," Marijuana for Medical Professionals Conference, Sep. 9-11, 2014, URL <http://www.theroc.us/images/gedde_presentation.pdf, Sep. 9-11, 2014>, 45 pages.
Gedde et al., "3.330: Whole Cannabis Extract of High Concentration Cannabidiol May Calm Seizures in Highly Refractory Pediatric Epilepsies," American Epilepsy Society, Dec. 2013, 449-450.
Geffrey et al., "Cannabidiol (CBD) Treatment for Refractory Epilepsy," American Epilepsy Society, Annual Meeting Abstract 2.427, 2014, retrieved on Feb. 10, 2017, URL <https://www.aesnet.org/meetings_events/annual_meeting_abstracts/view/1868979>, 2 pages.
Gloss, D., Vickrey, B.: "Cannabinoids for epilepsy (Review)", Cochrane Database of Systematic Reviews, 2014, 3.

(56) References Cited

OTHER PUBLICATIONS

Green [online], "CBD: An Unconventional Therapy," Nugs.com, Mar. 24, 2014, URL <http://nugs.com/article/cbd-an-unconventional-therapy.html>, 5 pages.
Gresham et al., "Treating Lennox-Gastaut syndrome in epileptic pediatric patients with third generation rufmamide," Neuropsychiatr Dis Treat, Oct. 5, 2010, 6:639-645.
Gross et al., "Marijuana use and Epilepsy: Prevalence in Patients of a Tertiary Care Epilepsy Center," Neurology, Jun. 8, 2004, 62(11):2095-2097.
Grotenhermen, "Epilepsiebehandlung des Angelman-Syndroms mit CBD (Cannabidiol) (Epilepsy treatment of Angelman syndrome with CBD (cannabidiol)," Angelman e.V., Jan. 2015, retrieved on Jun. 7, 2019, URL <http://s8a85e4d6fcfb04b6.jimcontent.com/download/version/1472724876/module/9873059694/name/Epilepsiebehandlung%20durch%20CBD.pdf>, 8 pages (with Machine translation).
Guerrini et al., "Lamotrigine and Seizure Aggravation in Severe Myoclonic Epilepsy," Epilepsia, 1998, 39(5):508-512.
Guimaraes et al., "Antianxiety effect of cannabidiol in the elevated plus-maze," Psychopharmacology, 1990, 100: 558-559.
GWPharm [online], "GW Pharmaceuticals Announces Epidiolex(R) Receives Fast Track Designation from FDA for the Treatment of Dravet Syndrome," GW Pharmaceuticals Press Release, Jun. 6, 2014, retrieved on Mar. 1, 2017, URL <https://www.gwpharm.com/about-us/news/gw-pharmaceuticals-announces-epidiolex%C2%AE-receives-fast-track-designation-fda-treatment>, 2 pages.
GWPharm [online], "GW Pharmaceuticals Announces Physician Reports of Epidiolex(R) Treatment Effect in Children and Young Adults with Treatment-resistant epilepsy from Physician-Led Expanded Access Treatment Program," GW Pharmaceuticals Press Release, Jun. 17, 2014, retrieved on May 1, 2017, URL <https://www.gwpharm.com/about-us/news/gw-pharmaceuticals-announces-physician-reports-epidiolex%C2%AE-treatment-effect-children>, 8 pages.
GWPharm [online], "GW Pharmaceuticals Announces Preliminary Results of Phase 2a Study for its Pipeline Compound GWP42006," GW Pharmaceuticals Press Release, Feb. 21, 2018, retrieved on Jun. 29, 2018, URL <https://www.gwpharm.com/about-us/news/gw-pharmaceuticals-announces-preliminary-results-phase-2a-study-its-pipeline-compound>, 5 pages.
GWPharm [online], "GW Pharmaceuticals Provides Update on Orphan Program in Childhood Epilepsy for Epidiolex®," GW Pharmaceuticals Press Release, Nov. 15, 2013, retrieved on Jun. 20, 2018, URL <https://www.gwpharm.com/about-us/news/gw-pharmaceuticals-provides-update-orphan-program-childhood-epilepsy-epidiolex%C2%AE>, 5 pages.
GWPharm [online], "GW Pharmaceuticals Receives Orphan Drug Designation by FDA for Epidiolex® in the Treatment of Lennox-Gastaut Syndrome," GW Pharmaceuticals Press Release, Feb. 28, 2014, retrieved on Feb. 10, 2017, URL <https://www.gwpharm.com/about-us/news/gw-pharmaceuticals-receives-orphan-drug-designation-fda-epidiolex%C2%AE-treatment-lennox>, 4 pages.
GWPharm [online], "Orphan Drug Designation Granted for Epidiolex in Dravet syndrome by the FDA—Seven Expanded Access INDs granted by FDA to US physicians to treat with Epidiolex 125 children suffering from intractable epilepsy syndromes," GW Pharmaceuticals Press Release, Nov. 15, 2013, retrieved on Feb. 10, 2017, URL <https://www.gwpharm.com/about-us/news/gw-pharmaceuticals-provides-update-orphan-program-childhood-epilepsy-epidiolex%C2%AE>, 5 pages.
Heinemann et al., "Chapter 4: An Overview of In Vitro Seizure Models in Acute and Organotypic Slices," Models of Seizures and Epilepsy, 2006 35-44.
Hill et al., "Cannabidivarin is anticonvulsant in mouse and rat," Br J Pharmacol, Dec. 2012, 167(8):1629-1642.
Hill et al., "$\Delta^9$-Tetrahydrocannabivarin suppresses in vitro epileptiform and in vivo seizure activity in adult rats," Epilepsia, Aug. 2010, 51(8):1522-1532.
Hill, "Cannabidivarin-rich cannabis extracts are anticonvulsant in mouse and rat via a CB1 receptor-independent mechanism," British Journal of Pharmacology, Oct. 2013, 170(3): 679-692.
Holmes et al. "Choosing the Correct AED: From Animal Studies to the Clinic,"Pediatr Neurol, Mar. 2008, 38(3): 151-162.
Iannotti et al., "Nonpsychotropic plant cannabinoids, cannabidivarin (CBDV) and cannabidiol (CBD), activate and desensitize transient receptor potential vanilloid 1 (TRPV1) channels in vitro: Potential for the treatment of neuronal hyperexcitability," ACS Chem. Neurosci., Jul. 16, 2014, 5:1131-1141.
ICE Epilepsy Alliance, The Dravet Syndrome Spectrum, Nov. 2008, 2 pages.
*INSYS Development Company, Inc.* v. *GW Pharma Limited and Otsuka Pharmaceutical Co., Ltd.*, Decision in IPR2017-00503, U.S. Pat. No. 9,066,920, dated Jul. 7, 2017, 26 pages.
*INSYS Development Company, Inc.* v. *GW Pharma Limited and Otsuka Pharmaceutical Co., Ltd.*, Declaration by Mark Polyakov, IPR2017-00503, U.S. Pat. No. 9,066,920, dated May 29, 2018, 1 page.
*INSYS Development Company, Inc.* v. *GW Pharma Limited and Otsuka Pharmaceutical Co., Ltd.*, Declaration of Professor Anthony G. Marson in IPR2017-00503, U.S. Pat. No. 9,066,920, dated Dec. 13, 2016, 28 pages.
*INSYS Development Company, Inc.* v. *GW Pharma Limited and Otsuka Pharmaceutical Co., Ltd.*, Declaration of Professor H. Steve White in IPR2017-00503, U.S. Pat. No. 9,066,920, dated Oct. 24, 2017, 69 pages.
*INSYS Development Company, Inc.* v. *GW Pharma Limited and Otsuka Pharmaceutical Co., Ltd.*, Declaration of Professor Leslie Benet in IPR2017-00503, U.S. Pat. No. 9,066,920, dated Nov. 22, 2016, 18 pages.
*INSYS Development Company, Inc.* v. *GW Pharma Limited and Otsuka Pharmaceutical Co., Ltd.*, Deposition of H. Steve White, dated Dec. 13, 2016, 50 pages.
*INSYS Development Company, Inc.* v. *GW Pharma Limited and Otsuka Pharmaceutical Co., Ltd.*, Final Written Decision in IPR2017-00503, U.S. Pat. No. 9,066,920, dated Jan. 3, 2019, 40 pages.
*INSYS Development Company, Inc.* v. *GW Pharma Limited and Otsuka Pharmaceutical Co., Ltd.*, Patent Owners' Preliminary Response in IPR2017-00503, U.S. Pat. No. 9,066,920, dated Apr. 11, 2017, 45 pages.
*INSYS Development Company, Inc.* v. *GW Pharma Limited and Otsuka Pharmaceutical Co., Ltd.*, Petition for Inter Partes Review, IPR2017-00503, U.S. Pat. No. 9,066,920, dated Dec. 16, 2016, 78 pages.
*INSYS Development Company, Inc.* v. *GW Pharma Limited and Otsuka Pharmaceutical Co., Ltd.*, Petitioner's Brief Regarding Ground III of the IPR, IPR2017-00503, U.S. Pat. No. 9,066,920, dated May 29, 2018, 45 pages.
*INSYS Development Company, Inc.* v. *GW Pharma Limited and Otsuka Pharmaceutical Co., Ltd.*, Petitioner's Reply to Patent Owner's Response, IPR2017-00503, U.S. Pat. No. 9,066,920, dated Jun. 19, 2018, 6 pages.
IUPHAR/BPS Guide to Pharmacology [online], "Entry for Δ9-tetrahydrocannabidiol," available on or before Mar. 29, 2016, retrieved on Jun. 20, 2018, URL <http://www.guidetopharmacology.org/GRAC/LigandDisplayForward?tab=biology&ligandId=242>, 2 pages.
Iuvone et al., "Neuroprotective Effect of Cannabidiol, a Nonpsychoactive Component From Cannabis Sativa, on β-amyloid-induced toxicity in PC12 Cells," J Neurochem, Apr. 2004, 89(1):134-41.
Izzo et al., "Non-psychotropic plant cannabinoids: new therapeutic opportunities from an ancient herb," Trends in Pharmacological Sciences, 2009, 30(10):515-527.
Jacobson and Porter, "Survey of Current Cannabidiol Use in Pediatric Treatment-Resistant Epilepsy", Apr. 2013, URL <https://www.thcint.com/uploads/1/9/3/7/19371199/cannabidiol_use_in_pediatric_epilepsy.pdf>, 1 page.
Jeavons et al., "Sodium Calproate in Treatment of Epilepsy," Br Med J., Jun. 15, 1974, 2(5919): 584-586.
Jones et al. [online], Info & Metrics / Article Information,"Cannabidiol Displays Antiepileptiform and Antiseizure Properties in

(56) References Cited

OTHER PUBLICATIONS

Vitro and in Vivo," J Pharmacol Exp Ther., Feb. 2010, 332(2): 569-577, retrieved on Jun. 25, 2018, URL: http://jpet.aspetjournals.org/content/332/2/569/tab-article-info, 9 pages.
Jones et al., "Cannabidiol Displays Antiepileptiform and Antiseizure Properties in Vitro and in Vivo," J Pharmacol Exp Ther., Feb. 2010, 332(2):559-577.
Joy et al., "Marijuana and Medicine: Assessing the Science Base", Institute of Medicine, National Academy Press, 1999, 170 pages.
Kahan et al., "Risk of Selection Bias in Randomized Trials," Trials, Sep. 2015, 16:405, 7 pages.
Kaplan, "F.D.A. Panel Recommends Approval of Cannabis-Based Drug for Epilepsy," NY Times, Apr. 19, 2018, retrieved on Jun. 20, 2018, URL <https://www.nytimes.com/2018/04/19/health/epidiolex-fda-cannabis-marajuana.html>, 3 pages.
Karler et al., "The anticonvulsant activity of cannabidiol and cannabinol," Life Science, 1973, 13: 1527-1531.
Karler et al., "The Cannabinoids as Potential Antiepileptics," J Clin Pharmacol., Aug.-Sep. 1981, 21:437S-448S.
Kelley et al., "Doose syndrome (myoclonic-astatic epilepsy): 40 years of progress," Developmental Medicine & Child Neurology, Aug. 2010, 52: 988-993.
Khan et al., "Key Attributes of TKDL: Laooq-e-Qinnab/Barai Zeequn-Nafs," Khazaain-al-Advia, 1911, 2 pages (with English translation).
Khan et al., "Key Attributes of TKDL: Nuskha-e-Qutoor," Muheet-e-Azam, 1887, 2 pages (with English translation).
Khan et al., "Key Attributes of TKDL: Sufoof-e-qinnab Barae Waja," Khazaain-al-Adiva, 1911, 5 pages (with English translation).
Khan et al., "Key Attributes of TKDL: Usaara-e-Qinnab Barai Qoolanj," Khazaain-al-Advia, 1911, 6 pages (with English translation).
Khan et al., "Key Attributes of TKDL: Zimad-e-qinnab," Khazaain-al-Adiva, 1911, 5 pages (with English translation).
Klitgaard et al., "Electrophysiological, neurochemical and regional effects of levetiracetam in the rat pilocarpine model of temporal lobe epilepsy," Seizure, Mar. 2003, 12(2):92-100.
Klitgaard et al., "Evidence for a unique profile of levetiracetam in rodent models of seizures and epilepsy," European J Pharm, Jul. 1998, 353(2):191-206.
Koppel et al.: "Systematic review: Efficacy and safety of medical marijuana in selected neurologic disorders" American Academy of Neurology, 2014, vol. 82, pp. 1556-1563.
Kramer et al., "Febrile infection-related epilepsy syndrome (FIRES): pathogenesis, treatment, and outcome: a multicenter study on 77 children," Epilepsia, Nov. 2011, 52(11):1956-1965.
Kruk-Słomka et al., "A comparison of mecamylamine and bupropion effects on memory-related responses induced by nicotine and scopolamine in the novel object recognition test in mice," Pharmacological Reports, Aug. 2014, 66(4): 638-646.
Kurz and Blass, "Use of dronabinol (delta-9-THC) in autism: a prospective single-case-study with an early infantile autistic child," 2010, Cannabinoids, 5(4): 4-6.
Kwan et al., "Definition of drug resistant epilepsy: consensus proposal by the ad hoc Task Force of the ILAE Commission on Therapeutic Strategies," Epilepsia, Jun. 2010, 51(6):1069-1077.
LaPrairie et al., "Cannabidiol is a negative allosteric modulator of the cannabinoid CB1 receptor," British J Pharmacology, 2015, 172(20): 4790-4805.
LeafScience.com [online], "What are the Highest CBD Strains?" Oct. 15, 2014, retrieved on Feb. 16, 2017, URL <www.leafscience.com/2014/10/15/highest-cbd-strains/>, 2 pages.
Leo et al., "Cannabidiol and epilepsy: Rationale and therapeutic potential," Pharamacological Research, Mar. 2016, 107: 85-92.
Lewis, "Mystery Mechanisms," TheScientist.com, Jul. 29, 2016, retrieved on Nov. 8, 2017, URL <https://www.the-scientist.com/?articles.view/articleNo/46688/title/Mystery-Mechanisms/>, 2 pages.
Lieu et al., "Assessment of self-selection bias in a pediatric unilateral hearing loss study," Otolaryngol Head Neck Surg, Mar. 2010, 142(3): 427-433.

Lindamood and Colasanti, "Effects of Δ9-Tetrahydrocannabinol and Cannabidiol on Sodium-Dependent High Affinity Choline Uptake in the Rat Hippocampus1," J Pharmacology Experimental Therapeutics, 1980, 213(2):216-221.
Long et al., "The Pharmacological actions of cannabidiol," Drugs of the Future, Jul. 2005, 30(7): 747-753.
Löscher and Schmidt, "Modem antiepileptic drug development has failed to deliver: ways out of the current dilemma." Epilepsia, Apr. 2011, 52(4):657-78.
Lowenstein "Chapter 363: Seizures and Epilepsy," Diseases of the Central Nervous System, 2008, 2498-2512.
Luttjohann et al., "A Revised Racine's scale for PTZ-induced seizures in rats," Physiology & Behavior, 2009, 98:579-586.
Lutz, "On-demand activation of the endocannabinoid system in the control of neuronal excitability and epileptiform seizures," Biochemical Pharmacology, Nov. 2004, 68(9):1691-1698.
Maa et al., "The Case for Medical Marijuana in Epilepsy," Epilepsia, Jun. 2014, 55(6):783-786.
Mackie, "Cannabinoid Receptors as Therapeutic Targets," Annu Rev Pharmacol Toxicol, 2006, 46:101-122.
Majoosi et al., "Key Attributes of TKDL: Saoot Baraae Sara," Kaamil-al-Sena'ah, Central Council for Research in Unani Medicine, 2005, 2 pages (with English translation).
Malfait et al., "The nonpsychoactive cannabis constituent cannabidiol is an oral anti-arthritic therapeutic in murine collagen-induced arthritis," PNAS, Aug. 15, 2000, 97(17):9561-9566.
Manni et al., "Obstructive Sleep Apnea in a Clinical Series of Adult Epilepsy Patients: Frequency and Features of the Comorbidity," Epilepsia, Jun. 2003, 44(6): 836-840.
Manno, "Status Epilepticus: Current Treatment Strategies," The Neurohospitalist, Jan. 2011, 1(1):23-31.
Mares et al., "Chapter 12: Electrical Stimulation-Induced Models of Seizures," Model of Seizures and Epilepsy, Asla Pitkänen, Philip A. Schwartzkroin & Solomon L. Moshé, eds., 2004, 153-159.
Martin et al., "Structure-Anticonvulsant Activity Relationships of Cannabidiol Analogs," National Institute on Drug Abuse, Research Monograph Series, 1987, 79:48-58.
Mattson et al., "Comparison of carbamazepine, phenobarbital, phenytoin, and primidone in partial and secondarily generalized tonic-clonic seizures," N Engl J Med, Jul. 18, 1985, 313(3):145-151.
Mattson et al., "Prognosis for total control of complex partial and secondary generalized tonic clonic seizures," Neurology, 1996, 47:68-76.
McCormick et al., "On the Cellular Network Bases of Epileptic Seizures," Annu Rev Physiol, 2001, 63:815-846.
McNamara, "Chapter 19: Pharmacotherapy of the Epilepsies,", Goodman & Gilman's The Pharmacological Basis of Therapeutics 11th ed., McGraw-Hill Companies, 2006, 501-525.
Mechoulam et al., "Cannabidiol: An Overview of Some Pharmacological Aspects," J Clin Pharmacol, 2002, 42:11S-19S.
Mechoulam et al., "Toward drugs derived from cannabis," Naturwissenschaften, Apr. 1978, 65(4): 174-179.
Medicines Q&As: Cannabis-based medicinal products—potential drug interactions, Prepared by UK Medicines Information (UKMi) pharmacists for NHS healthcare professionals, Nov. 29, 2018.
Medicos [online], "Convulsive Disorders and Their Interference with Driving," Medicos, 2014, retrieved Feb. 10, 2017, URL <https://www.medicosporlaseguridadvial.com/en/clinical-subjects/neurologic-diseases/convulsive-disorders-and-their-interference-with-driving/>, 3 pages.
Merlis, "Proposal for an International Classification of the Epilepsies," Epilepsia, 1970, 11:114-119.
Miller et al., "Mapping genetic modifiers of survival in a mouse model of Dravet syndrome," Genes, Brain and Behavior, 2014, 13:163-172.
Moral et al., "Pipeline on the Move," Drugs of the Future, Jan. 2014, 39(1): 49-56.
Morard et al., "Conversion to Sirolimus-Based Immunosuppression in Maintenance Liver Transplantation Patients," Liver Transplantation, 2007, 13:658-664.
MyVirtualMedicalCentre [online], "Aicardi syndrome," mvmc.com, Feb. 2004, retrieved on Jan. 25, 2019, https://www.myvmc.com/diseases/aicardi-syndrome/, 6 pages.

(56) References Cited

OTHER PUBLICATIONS

Neto et al., "The role of polar phytocomplexes on anticonvulsant effects of leaf extracts of Lippia Alba (Mill.) N.E. Brown chemotypes," J. Pharm Pharmacol, 2009, 61(7):933-939.

Ng et al., "Illicit Drug Use and the Risk of New-Onset Seizures," Am J Epidemiol, 1990, 132(1):47-57.

Oakley et al., "Dravet Syndrome Insights into pathophysiology and therapy from a mouse model of Dravet syndrome," Epilepsia, Apr. 2011, 52(Suppl. 2): 59-61.

Obay et al., "Antiepileptic effects of ghrelin on pentylenetetrazole-induced seizures in rats," Peptides, Jun. 2007, 28(6):1214-1219.

PCT International Preliminary Report on Patentability in International Appln. No. PCT/GB2010/051066, dated Jun. 9, 2011, 6 pages.

PCT International Preliminary Report on Patentability in International Appln. No. PCT/GB2012/052284, dated Dec. 12, 2013, 12 pages.

PCT International Preliminary Report on Patentability in International Appln. No. PCT/GB2015/051775, dated Aug. 10, 2016, 9 pages.

PCT International Preliminary Report on Patentability in International Appln. No. PCT/GB2015/053030, dated Apr. 18, 2017, 6 pages.

PCT International Preliminary Report on Patentability in International Appln. No. PCT/GB2016/051792, dated Sep. 1, 2017, 14 pages.

PCT International Preliminary Report on Patentability in International Appln. No. PCT/US2017/050868, dated Oct. 11, 2018, 7 pages.

PCT International Search Report and Written Opinion in International Appln. No. PCT/GB2010/051066 dated Dec. 13, 2010, 8 pages.

PCT International Search Report and Written Opinion in International Appln. No. PCT/GB2011/050649, dated May 30, 2011, 15 pages.

PCT International Search Report and Written Opinion in International Appln. No. PCT/GB2012/052284, dated Nov. 16, 2012, 11 pages.

PCT International Search Report and Written Opinion in International Appln. No. PCT/GB2015/051775, dated Aug. 26, 2015, 11 pages.

PCT International Search Report and Written Opinion in International Appln. No. PCT/GB2015/051776, dated Aug. 25, 2015, 11 pages.

PCT International Search Report and Written Opinion in International Appln. No. PCT/GB2016/052340, dated Oct. 25, 2016, 12 pages.

PCT International Search Report and Written Opinion in International Appln. No. PCT/GB2017/051913, dated Sep. 15, 2017, 9 pages.

PCT International Search Report and Written Opinion in International Appln. No. PCT/GB2017/051914, dated Sep. 12, 2017, 10 pages.

PCT International Search Report and Written Opinion in International Appln. No. PCT/GB2017/053735, dated Mar. 14, 2018, 14 pages.

PCT International Search Report and Written Opinion in International Appln. No. PCT/US2017/050868, dated Aug. 6, 2017, 14 pages.

PCT International Search Report and Written Opinion in International Appln. PCT/GB2017/051943, dated Sep. 12, 2017, 10 pages.

PCT International Search Report in International Appln. No. PCT/GB2012/050002, dated Feb. 24, 2012, 3 pages.

Pelliccia et al. [online], "Treatment with CBD in oily solution of drug-resistant paediatric epilepsies," 2005 Congress on Cannabis and the Cannabinoids, Leiden, The Netherlands: International Association for Cannabis as Medicine, 2005, 14, retrieved on Jun. 30, 2015, URL <http://www.cannabis-med.org/studies/ww_en_db_study_show.php?s_id=173&&search_pattern=EPILEPSY>, 2 pages, Abstract only.

Pereira et al., "Study pharmacologic of the GABAergic and glutamatergic drugs on seizures and status epilepticus induced by pilocarpine in adult Wistar rats," Neurosci Lett, Jun. 2007, 419(3): 253-257.

Pertwee, "Cannabinoid receptor ligands: clinical and neuropharmacological considerations, relevant to future drug discovery and development," Expert Opin Investig Drugs, Jul. 2000, 9(7): 1553-1571.

Pertwee, "Chapter 3: The Pharmacology and Therapeutic Potential of Cannabidiol," Cannabinoids, Ed Vincenzo Di Marzo ed., 2004, 32-83.

Pertwee, "The diverse CB1 and CB2 receptor pharmacology of three plant cannabinoids: $\Delta 9$-tetrahydrocannabinol, cannabidiol and $\Delta 9$-tetrahydrocannabivarin," Br. J. Pharmacol, 2008, 153(2):199-215.

Perucca, "Clinically relevant drug interactions with antiepileptic drugs", British Journal of Clinical Pharmacology, 2005, vol. 61, No. 3, p. 246-255.

Perucca, "Pharmacologic Advantages of Antiepileptic Drug Monotherapy", Epilepsia, 1997, vol. 35, No. 5, pp. S6-S8.

Petrocellis et al., "Effects of cannabinoids and cannabinoid-enriched Cannabis extracts on TRP channels and endocannabinoid metabolic enzymes," British Journal of Pharmacology, 2011, 163: 1479-1494.

Physician's Desk Reference, 63rd Ed., 2009, 423-431, 2192-2194, 2639-2242, 3019-3022.

Pisani, "Influence of co-medication on the metabolism of valproate", Pharmaceutish Weekblad Scientific Edition, 1992, vol. 14, No. 3A, p. 108-113.

Pohl et al., "Effects of flunarizine on Metrazol-induced seizures in developing rats," Epilepsy Res, 1987, 1:302-305.

Poortman-van der Meer, "A contribution to the improvement of accuracy in the quantitation of THC," Forensic Science International, Apr. 1999, 101(1): 1-8.

Porter et al., "Randomized, multicenter, dose-ranging trial of retigabine for partial-onset seizures," Neurology, Apr. 2007, 68(15): 1197-1204.

Porter et al., "Report of a Parent Survey of Cannabidiol-enriched Cannabis use in Pediatric Treatment-resistant Epilepsy," Epilepsy Behavior, Dec. 2013, 29(3): 574-577.

Potter, "Chapter 4: Cannabis Horticulture," Handbook of Cannabis, ed. Roger G. Pertwee, 2014, 65-88.

Pouton, "Lipid formulations for oral administration of drugs: non-emulsifying, self-emulsifying and 'self-microemulsifying' drug delivery systems," Eur. J Pharm Sci, Oct. 2000, 11(Supp. 2): S93-S98.

Press et al., "Parental reporting of response to oral cannabis extracts for treatment of refractory epilepsy," Epilepsy Behav, Apr. 2015, 45:49-52.

Pruitt et al., "Ethanol in Liquid Preparations Intended for Children," Padiatrics, Mar. 1984: 73(3): 405-407.

Rabinski [online], "CBD-A: Cannabidiol Acid Cannabinoid Profile," MassRoots, Jul. 2, 2015, retrieved on Jan. 31, 2018, URL <https://www.massroots.com/learn/can-the-cbd-a-cannabinoid-help-you/>, 4 pages.

Ramantani et al., "Epilepsy in Aicardi—Goutieres syndrome," Official J Eur Paediatric Neurology Society, 2014, 18: 30-37.

Rauca et al., "The role of superoxide dismutase and a-tocopherol in the development of seizures and kindling induced by pentylenetetrazol—influence of the radical scavenger a-phenyl-N-tert-butyl nitrone," Brain Research, May 29, 2004, 1009(1-2):203-212.

Resstel et al., "5-HT1A receptors are involved in the cannabidiol-induced attenuation of behavioural and cardiovascular responses to acute restraint stress in rats," Br J Pharmacol, Jan. 2009, 156(1): 181-188.

Rosenberg et al., "Cannabinoids and Epilepsy," Neurotherapeutics, Oct. 2015, 12(4): 747-768.

Rosenkrantz et al., "Oral and Parenteral Formulations of Marijuana Constituents," J Pharm Sci, Jul. 1972, 61(7)1106-1112.

Rubio et al., "In Vivo Experimental Models of Epilepsy," Central Nervous System Agents in Medicinal Chemistry, 2010, 10:298-309.

Russo, "Taming THC: potential cannabis synergy and phytocannabinoid-terpenoid entourage effects," British J. of Pharm, 2011, 163:1344-1364.

(56) References Cited

OTHER PUBLICATIONS

Sadanandasarma et al., "Key Attributes of TKDL: Suddha Bhanga Visista Gunah Aur Matra," Rasatarangini 11th Ed., 1979:720-723 (with English translation).
SalutarisDrops.com [online], "Cannabidiol for Aicardi Syndrome," Salutaris, available on or before Oct. 2014, retrieved on Feb. 10, 2017, URL <http://web.archive.org/web/20141012220050/http://salutarisdrops.com/cannabidiol-aicardi-syndrome/>, 3 pages.
Sander, "The epidemiology of epilepsy revisited," Curr Opin Neurol, Apr. 2003, 16(2):165-170.
Sandyk et al., "Preliminary trial of cannabidiol in Huntington's Disease," Marihuana: An International Research Report, 1988, 157-162.
Sastri et al., "Key Attributes of TKDL: Vijaya Kalpah (Apasmaranasaka)," Anandakandam 1st ed., 1952:241, 5 pages (with English translation).
Scuderi et al., "Cannabidiol in Medicine: A Review of its Therapeutic Potential in CNS Disorders," Phytother Res, May 2009, 23(5):597-602.
Shukla [online], "New Automated Purification Strategies for Scale-Up," PCISyntesis.com, posted Dec. 25, 2017, https://www.pcisynthesis.com/new-automated-purification-strategies-for-scale-up/, 5 pages.
Silva et al., "Clobazam as Add-on Therapy in Children with Epileptic Encephalopathy," Can J Neurol Sci, 2006 33: 209-213.
Sperling et al., "Carisbamate as adjunctive treatment of partial onset seizures in adults in two randomized, placebo-controlled trials," Epilepsia, Mar. 2010, 51(3):333-343.
Stafstrom et al., "Models of Pediatric Epilepsies: Strategies and Opportunities," Epilepsia, 2006, 47(8): 1407-1414.
Stephenson, "In Memoriam: Professor Jean Aicardi (1926-2015)," Pediatric Neurology, Jan. 2016, 54: 3-4.
Stott et al., "Cannabinoids for the pharmaceutical industry," Euphytica, 2004, 140:83-93.
Strickley, "Solubilizing Excipients in Oral and Injectable Formulations," Table VIII, Pharmaceutical Research, Feb. 2004, 21(2): 201-230.
Swann., "The Effects of Seizures on the Connectivity and Circuitry of the Developing Brain," MRDD, 2004, 10(2):96-100.
Thomas et al., "Cannabidiol displays unexpectedly high potency as an antagonist of CB1 and CB2 receptor agonists in vitro," British J Pharmacology, 2007, 150(5): 613-623.
Thomas et al., "Evidence that the Plant Cannabinoid Δ9-Tetrahydrocannabivarin is a Cannabinoid CBI and CB2 Receptor antagonist," Br J Pharmacol, Dec. 2005, 146(7):917-926.
Thumma et al., "Influence of plasticizers on the stability and release of a prodrug of Δ9-tetrahydrocannabinol incorporated in poly(ethylene oxide) matrices," Eur J Pharmceutics and Biopharmaceutics, Oct. 2008, 70(2): 605-614.
Thurman et al., "Standards for epidemiologic studies and surveillance of epilepsy," Epilepsia, Sep. 2011, 52 Suppl 7: 2-26.
Thurstone, "Avoid Charlotte's Web for Epilepsy," Jun. 26, 2014, URL <http://drthurstone.com/charlotted-web-not-safest-option-epiliepsy-trealment/>, 4 pages.
Trembly and Sherman, "Double-blind clinical study of cannabidiol as a secondary anticonvulsant," Marijuana '90 Int. Conf. on Cannabis and Cannabinoids, Kolympari (Crete), Jul. 8-11, 1990, 1 page, Abstract Only.
Turkanis et al., "An Electrophysiological Analysis of the Anticonvulsant Action of Cannabidiol on Limbic Seizures in Conscious Rats," Epilepsia, 1979, 20:351-363.
U.S. Department of Health and Human Services, Food and Drug Administration Center for Drug Evaluation and Research (CDER), "Guidance for Industry Estimating the Maximum Safe Starting Dose in Initial Clinical Trials for Therapeutics in Adult Healthy Volunteers," Jul. 2005, 30 pages.
Unimed Pharmaceuticals, Inc., "Marinol®," Jul. 2006 <https://www.accessdata.fda.gov/drugsatfda_docs/label/2006/018651s025s0261b1.pdf>, 11 pages.

Usami et al., "Synthesis and Pharmacological Evaluation in Mice of Halogenated Cannabidiol Derivatives," Chem Pharm Bull, Nov. 1999, 47(11):1641-1645.
USPTO Information Disclosure Statement Form PTO-1449 in U.S. Appl. No. 13/380,305, dated Nov. 24, 2014, 8 pages.
USPTO Notice of Allowance in U.S. Appl. No. 13/380,305, dated Dec. 10, 2014, 5 pages.
USPTO Notice of Allowance in U.S. Appl. No. 13/380,305, dated Mar. 19, 2015, 7 pages.
USPTO Office Action in U.S. Appl. No. 13/380,305, dated Aug. 25, 2014, 6 pages.
USPTO Request for Continued Examination with the Amendment and Information Disclosure Statement in U.S. Appl. No. 13/380,305, filed Mar. 2, 2015, 8 pages.
USPTO Third Preliminary Amendment under 37 C.F.R. 1.115 in U.S. Appl. No. 13/380,305, dated May 23, 2014, 4 pages.
Utah.gov [online], "2nd Agenda Controlled Substances Advisory Committee Meeting," Nov. 12, 2013, URL <https://www.utah.gov/pmn/files/81459.pdf>, 63 pages.
Van Rijckevorsel, "Treatment of Lennox-Gastaut Syndrome: overview and recent findings," Neuropsychiatr Dis Treat, Dec. 2008, 4(6): 1001-1019.
Velisek, "Chapter 11: Models of Chemically-Induced Acute Seizures," Models of Seizures and Epilepsy, 2006, 127-152.
Veliskova, "Chapter 48: Behavioral Characterization of Seizures in Rats," Models Seizures Epilepsy, 2006, 601-611.
Vietnam Office Action in Application No. 1201400886, dated Sep. 24, 2019, 2 pages, English Translation.
Vollner et al., "Haschisch XX+ [Haschiscc XX+]: Cannabidivarin, a new hashish substance," Tetrahedron Letters, 1969, 10(3):145-147.
Wahle et al., "Development of Tolerance to the Anticonvulsant Effect of Valproate but not to Ethosuximide in a Rat Model of Absence Epilepsy," Eur J Pharma, May 1990, 181(1-2): 1-8.
Wallace et al., "Assessment of the role of CB1 receptors in cannabinoid anticonvulsant effects," European J Pharmacology, 2001, 428(1):51-57.
Wallace et al., "Pharmacotherapy for Dravet syndrome," Pediatr. Drugs, Jun. 2016, 18:197-208.
Weston et al., "Tetrahydrocannabivarin Exhibits Anticonvulsant Effects in a Piriform Cortical Brain Slice Model of Epileptiform Activity," Proceedings of the British Pharm Society, Dec. 2006, retrieved on Mar. 1, 2017, URL <http://www.pA2online.org/abstract/abstract.jsp?abid=28533>, 1 page, Abstract Only.
Wikipedia.org [online], "Cannabinoid," Wikipedia, Apr. 2003, retrieved on Mar. 1, 2017, URL <https://en.wikipedia.org/wiki/Cannabinoid>, 15 pages.
Wingerchuk, "Cannabis for medical purposes: cultivating science, weeding out the fiction," Lancent, Jul. 2004, 364:315-316.
Yu et al., "Reduced sodium current in GABAergic interneurons in a mouse model of severe myoclonic epilepsy in infancy," Nature Neuroscience, Sep. 2006, 9(9): 1142-1149.
Yuriev, "Endogenic Cannabinoid System is a New Perspective Object of Pharmacotherapeutic Effect to Disease of Nervous System," Ukrainsky Metodichny Chasopis, 2005, 6(50): 21-29 (with English Abstract).
Zamberletti et al., "Alterations of prefrontal cortex GABAergic transmission in the complex psychotic-like phenotype induced by adolescent delta-9-tetrahydrocannabinol exposure in rats," Neurobiology of Disease, Mar. 2014, 63: 35-47.
Zhao et al., "Chapter 27: Repetitive Seizures in the Immature Brain," Models of Seizures and Epilepsy, 2006, 341-350.
Zhornitsky and Potvin, "Cannabidiol in Humans—The Quest for Therapeutic Targets," Pharmaceuticals, 2012, 5:529-552.
Zuardi et al., "Cannabidiol, a Cannabis sativa constituent, as an antipsychotic drug," Brazilian Journal of Medicine and Biological Research, Apr. 2006, 39(4): 421-429.
Zuardi et al., "Cannabidiol: from an inactive cannabinoid to a drug with wide spectrum of action," Rev Bras Psiquiatr, 2008, 30(3): 271-80.

* cited by examiner

Maximum seizure severity of the CBDV (-/-) BDS in the PTZ model of epilepsy

Percentage mortality of the CBDV (-/-) BDS in the PTZ model of epilepsy

Percentage of animals that were seizure free in the CBDV (-/-) BDS in the PTZ model of epilepsy Latency to seizure onset in the CBDV (-/-) BDS in the PTZ model of epilepsy Percentage of animals that experienced tonic-clonic seizures in the CBDV (-/-) BDS in the PTZ model of epilepsy

PHARMACEUTICAL COMPOSITION COMPRISING THE PHYTOCANNABINOIDS CANNABIDIVARIN (CBDV) AND CANNABIDIOL (CBD)

CROSS-REFERENCE TO RELATED APPLICATIONS

This is a continuation of U.S. patent application Ser. No. 14/345,968, filed Mar. 20, 2014, which is a 35 U.S.C. § 371 National Stage Application of International Application No. PCT/GB2012/052284, filed Sep. 14, 2012, which claims priority to United Kingdom Application No. 1116789.7, filed Sep. 29, 2011. The entire content of each of these applications is hereby incorporated herein by reference.

This invention relates to a pharmaceutical composition comprising or consisting essentially of the phytocannabinoids cannabidivarin (CBDV) and cannabidiol (CBD).

The composition is particularly safe and efficacious for use in the treatment of neurological conditions, characterized by hyper-excitability of the central nervous system, convulsions or seizures such as occur in epilepsy.

Preferably the CBDV and the CBD are present with at least one non-cannabinoid component of *cannabis* such as one or more terpenes or a terpene fraction.

More particularly the composition further comprises one or more cannabichromene type compounds. Particularly cannabichromene propyl variant (CBCV) and/or cannabichromene (CBC).

More particularly still the composition is absent or substantially absent of other cannabinoids, including in particular tetrahydrocannabinol (THC) and tetrahydrocannabivarin (THCV), which would normally be present in significant amounts in *cannabis* chemotypes bred to contain a significant amount of CBDV and/or CBD.

BACKGROUND

Epilepsy is a chronic neurological disorder presenting a wide spectrum of diseases that affects approximately 50 million people worldwide (Sander, 2003). Advances in the understanding of the body's internal 'endocannabinoid' system has lead to the suggestion that *cannabis*-based medicines may have the potential to treat this disorder of hyper-excitability in the central nervous system (Mackie, 2006, Wingerchuk, 2004, Alger, 2006).

*Cannabis* has been ascribed both pro-convulsant (Brust et al., 1992) and anti-convulsant effects. Therefore, it remains to determine whether cannabinoids represent a yet to be unmasked therapeutic anticonvulsant or, conversely, a potential risk factor to recreational and medicinal users of *cannabis* (Ferdinand et al., 2005).

In 1975 Consroe et al. described the case of young man whose standard treatment (phenobarbital and phenytoin), didn't control his seizures. When he began to smoke *cannabis* socially he had no seizures. However when he took only *cannabis* the seizures returned. They concluded that 'marihuana may possess an anti-convulsant effect in human epilepsy'.

A study by Ng (1990) involved a larger population of 308 epileptic patients who had been admitted to hospital after their first seizure. They were compared to a control population of 294 patients who had not had seizures, and it was found that using *cannabis* seemed to reduce the likelihood of having a seizure. However this study was criticized in an Institute of Medicine report (1999) which claimed it was 'weak', as 'the study did not include measures of health status prior to hospital admissions and differences in their health status might have influenced their drug use' rather than the other way round.

Three controlled trials have investigated the anti-epilepsy potential of cannabidiol. In each, cannabidiol was given in oral form to sufferers of generalised grand mal or focal seizures.

Cunha et al (1980) reported a study on 16 grand mal patients who were not doing well on conventional medication. They received their regular medication and either 200-300 mg of cannabidiol or a placebo. Of the patients who received CBD, 3 showed complete improvement, 2 partial, 2 minor, while 1 remained unchanged. The only unwanted effect was mild sedation. Of the patients who received the placebo, 1 improved and 7 remained unchanged.

Ames (1986) reported a less successful study in which 12 epileptic patients were given 200-300 mg of cannabidiol per day, in addition to standard antiepileptic drugs. There seemed to be no significant improvement in seizure frequency.

Trembly et al (1990) performed an open trial with a single patient who was given 900-1200 mg of cannabidiol a day for 10 months. Seizure frequency was markedly reduced in this single patient.

In addition to the disclosures suggesting CBD may be beneficial there is a report (Davis & Romsey) of tetrahydrocannabinol (THC) being administered to 5 institutionalized children who were not responding to their standard treatment (phenobarbital and phenoytin). One became entirely free of seizures, one became almost completely free of seizures, and the other three did no worse than before.

In WO 2006/054057 it is suggested that the cannabinoid tetrahydrocannabivarin (THCV) may behave as anti-epileptic. However the main teaching in this document is the determination that THCV acts as a CB1 antagonist.

The application WO 2007/138322 shows CBD to be an inverse agonist at the CB1 and CB2 receptors and suggests this compound and structurally related compounds including CBDV, may have a therapeutic benefit in a wide range of conditions which involve these receptors. More specifically the data demonstrates that the cannabinoid CBD reduced bodyweight in rats.

However other work on cannabinoids has shown that despite THCV's structural similarity to THC the two compounds behave quite differently at the CB1 receptor and consequently it does not follow that the propyl cannabinoid analogs will behave as their pentyl equivalents.

In addition a study in 2007 by Deshpande et al. established that the CB1 antagonist rimonabant was a pro-convulsant; this study demonstrated that antagonism of the CB1 receptor caused epileptic activity. The inference from this study is that cannabinoids which act as antagonists of the CB1 receptor may not be useful as anti-convulsants; indeed they may exacerbate such a condition.

The application WO 2007/083098 describes the use of *cannabis* plant extracts with neuroprotective properties. Cannabinoid extracts containing THC and CBD were shown to be more effective than their pure counterparts in this area of medicine.

The application WO 02/064109 describes a pharmaceutical formulation where the cannabinoids THC and CBD are used. The application goes on to state that the propyl analogs of these cannabinoids may also be used in the formulation. Since this application was written it has been shown that THCV behaves in a very different manner to THC and therefore the assumption that the propyl analogs of cannabinoids may behave in a similar manner to their pentyl counterparts is now not valid.

The application GB2471565 describes the use of THCV for the treatment of generalised seizures; it also describes the use of CBD in combination with THCV.

The application GB1005364.3 (unpublished) describes the use of CBDV for use in the treatment of epilepsy.

The condition of epilepsy is a very difficult to treat disease, there are more than forty recognisable types of epileptic syndrome partly due to seizure susceptibility varying from patient to patient (McCormick and Contreras, 2001, Lutz, 2004) and a challenge is finding drugs which are effective against these differing types.

Neuronal activity is a prerequisite for proper brain function. However, disturbing the excitatory—inhibitory equilibrium of neuronal activity may induce epileptic seizures. These epileptic seizures can be grouped into two basic categories:
  a) partial, and
  b) generalised seizures.

Partial seizures originate in specific brain regions and remain localised—most commonly the temporal lobes (containing the hippocampus), whereas generalised seizures appear in the entire forebrain as a secondary generalisation of a partial seizure (McCormick and Contreras, 2001, Lutz, 2004). This concept of partial and generalised seizure classification did not become common practice until the International League Against Epilepsy published a classification scheme of epileptic seizures in 1969 (Merlis, 1970, Gastaut, 1970, Dreifuss et al., 1981).

The International League Against Epilepsy further classified partial seizures, separating them into simple and complex, depending on the presence or the impairment of a consciousness state (Dreifuss et al., 1981).

The League also categorized generalised seizures into numerous clinical seizure types, some examples of which are outlined below:

Absence seizures occur frequently, having a sudden onset and interruption of ongoing activities. Additionally, speech is slowed or impeded with seizures lasting only a few seconds (Dreifuss et al., 1981).

Tonic-clonic seizures, often known as "grand mal", are the most frequently encountered of the generalised seizures (Dreifuss et al., 1981). This generalised seizure type has two stages: tonic muscle contractions which then give way to a clonic stage of convulsive movements. The patient remains unconscious throughout the seizure and for a variable period of time afterwards.

Atonic seizures, known as "drop attacks", are the result of sudden loss of muscle tone to either a specific muscle, muscle group or all muscles in the body (Dreifuss et al., 1981).

The onset of epileptic seizures can be life threatening with sufferers also experiencing long-term health implications (Lutz, 2004). These implications may take many forms:
  mental health problems (e.g. prevention of normal glutamatergic synapse development in childhood);
  cognitive deficits (e.g. diminishing ability of neuronal circuits in the hippocampus to learn and store memories); and
  morphological changes (e.g. selective loss of neurons in the CA1 and CA3 regions of the hippocampus in patients presenting mesial temporal lobe epilepsy as a result of excitotoxicity) (Swann, 2004, Avoli et al., 2005)

It is noteworthy that epilepsy also greatly affects the lifestyle of the sufferer—potentially living in fear of consequential injury (e.g. head injury) resulting from a grand mal seizure or the inability to perform daily tasks or the inability to drive a car unless having had a lengthy seizure-free period (Fisher et al., 2000).

Despite the historic work on CBD in epilepsy in the 1980's/1990's, research in the field of anti-convulsants has focused on many other candidates many of which are now approved for use in the treatment of epilepsy. Such drugs include: acetozolamide, carbamazepine, clobazam, clonazepam, ethosuximide, eslicarbazepine acetate, gabapentin, lacosamide, lamotriquine, levetiracetam, oxcarbazepine, phenobarbital, phenytoin, pregabalin, primidone, rufinamide, sodium valproate, tiagabine, topiramate, valproate, vigabatrin, and zonisamide.

The mode of action of some of these is understood and for others is unknown. Some modes of action are set out in Table 1 below: (Adapted from: Schachter S C. Treatment of seizures. In: Schachter S C, Schomer D L, eds. The comprehensive evaluation and treatment of epilepsy. San Diego, Calif.: Academic Press; 1997. p. 61-74)

TABLE 1

| Antiepileptic drug | Mechanism of action | Sodium or calcium or GABA channel involvement |
|---|---|---|
| Barbiturates: primidone (Mysoline), phenobarbital | Enhances GABAergic inhibition | GABA |
| Carbamazepine (Tegretol, Tegretol-XR, Carbatrol) | Inhibits voltage-dependent sodium channels | Sodium |
| Ethosuximide (Zarontin) | Modifies low-threshold or transient neuronal calcium currents | Calcium |
| Felbamate (Felbatol) | Unknown | |
| Gabapentin (Neurontin) | Unknown | |
| Lamotrigine (Lamictal) | Inhibits voltage-dependent sodium channels, resulting in decreased release of the excitatory neurotransmitters glutamate and aspartate | Sodium |
| Phenytoin (Dilantin, Phenytek) | Blocks sodium-dependent action potentials; reduces neuronal calcium uptake | Sodium/Calcium |
| Valproate (Depakote, Depakote ER, Depakene, valproic acid) | Reduces high-frequency neuronal firing and sodium-dependent action potentials; enhances GABA effects | Sodium/GABA |

However despite the introduction of some twenty different compounds for treatment of epilepsy over the last twenty years there remains a need for alternate drugs for several reasons:

i) 1-2% of the world's population suffer from epilepsy (http://www.ncbi.nlm.nih.gov/sites/ppmc/articles/PMC1808496/);
ii) Of these 30% are refractory to existing treatments; and
iii) There are also notable motor side effects in the existing therapies (http://en.wikipedia.orq/wiki/Epilepsy).

For example valproate and ethosuximide both exhibit notable motor and other side effects (including sedation) when given to rats at doses greater than 200 mg/kg, as does phenobarbital at doses greater than 250 mg/kg in rat models of epilepsy.

Three well-established and extensively used in vivo models of epilepsy are:

pentylenetetrazole-induced (PTZ) model of generalised seizures (Obay et al., 2007, Rauca et al., 2004);
pilocarpine-induced model of temporal lobe (i.e. hippocampus) seizures (Pereira et al., 2007); and
penicillin-induced model of partial seizures (Bostanci and Bagirici, 2006).

These provide a range of seizure and epilepsy models, essential for therapeutic research in humans.

In the foregoing specification the following terms are used and are intended to have the following meanings/definitions:

"Cannabinoids" are a group of compounds including the endocannabinoids, the phytocannabinoids and those which are neither endocannabinoids or phytocannabinoids, hereafter "syntho-cannabinoids".

"Endocannabinoids" are endogenous cannabinoids, which are high affinity ligands of CB1 and CB2 receptors.

"Phytocannabinoids" are cannabinoids that originate in nature and can be found in the *cannabis* plant. The phytocannabinoids can be present in an extract including a botanical drug substance, isolated, or reproduced synthetically.

"Syntho-cannabinoids" are those compounds capable of interacting with the cannabinoid receptors (CB1 and/or CB2) but are not found endogenously or in the *cannabis* plant. Examples include WIN 55212 and rimonabant.

An "isolated phytocannabinoid" is one which has been extracted from the *cannabis* plant and purified to such an extent that all the additional components such as secondary and minor cannabinoids and the non-cannabinoid fraction have been removed.

A "synthetic cannabinoid" is one which has been produced by chemical synthesis this term includes modifying an isolated phytocannabinoid, by for example forming a pharmaceutically acceptable salt thereof.

A "botanical drug substance" or "BDS" is defined in the Guidance for Industry Botanical Drug Products Draft Guidance, August 2000, US Department of Health and Human Services, Food and Drug Administration Centre for Drug Evaluation and Research as: "A drug derived from one or more plants, algae, or microscopic fungi. It is prepared from botanical raw materials by one or more of the following processes: pulverisation, decoction, expression, aqueous extraction, ethanolic extraction or other similar processes." A botanical drug substance does not include a highly purified or chemically modified substance derived from natural sources. Thus, in the case of *cannabis*, BDS derived from *cannabis* plants do not include highly purified Pharmacopoeial grade cannabinoids.

In the present invention a BDS is considered to have two components: the phytocannabinoid-containing component and the non-phytocannabinoid containing component. Preferably the phytocannabinoid-containing component is the larger component comprising greater than 50% (w/w) of the total BDS and the non-phytocannabinoid containing component is the smaller component comprising less than 50% (w/w) of the total BDS.

The amount of phytocannabinoid-containing component in the BDS may be greater than 55%, through 60%, 65%, 70%, 75%, 80% to 85% or more of the total extract. The actual amount is likely to depend on the starting material used and the method of extraction used.

The "principle phytocannabinoid" in a BDS is the phytocannabinoid that is present in an amount that is higher than that of the other phytocannabinoids. Preferably the principle phytocannabinoid is present in an amount greater than 40% (w/w) of the total extract. More preferably the principle phytocannabinoid is present in an amount greater than 50% (w/w) of the total extract. More preferably still the principle phytocannabinoid is present in an amount greater than 60% (w/w) of the total extract.

The amount of the principle phytocannabinoid in the BDS is preferably greater than 50% of the phytocannabinoid-containing fraction, more preferably still greater than 55% of the phytocannabinoid-containing fraction, and more preferably still greater than 60% through 65%, 70%, 75%, 80%, 85%, 90% and 95% of the phytocannabinoid-containing fraction.

The "secondary phytocannabinoid/s" in a BDS is the phytocannabinoid/s that is/are present in significant proportions. Preferably the secondary phytocannabinoid is present in an amount greater than 5% (w/w) of the total extract, more preferably greater than 10% (w/w) of the total extract, more preferably still greater than 15% (w/w) of the total extract. Some BDS's will have two or more secondary phytocannabinoids that are present in significant amounts. However not all BDS's will have a secondary phytocannabinoid.

The "minor phytocannabinoid/s" in a BDS can be described as the remainder of all the phytocannabinoid components once the principle and secondary phytocannabinoids are accounted for. Preferably the minor phytocannabinoids are present in total in an amount of less than 5% (w/w) of the total extract, and most preferably the minor phytocannabinoid is present in an amount less than 2% (w/w) of the total extract.

The term "absent" or "substantially absent" refers to less than 1%, preferably less than 0.5%, more preferably still less than 0.3%, most preferably less than 0.1% (w/w) of total extract.

The term "consisting essentially of" is limited to the phytocannabinoids which are specified, it does not exclude non-cannabinoid components that may also be present.

Typically the non-phytocannabinoid containing component of the BDS comprises terpenes, sterols, triglycerides, alkanes, squalenes, tocopherols and carotenoids.

These compounds may play an important role in the pharmacology of the BDS either alone or in combination with the phytocannabinoid.

The "terpene fraction" may be of significance and can be broken down by the type of terpene: monoterpene or sesquiterpene. These terpene components can be further defined in a similar manner to the cannabinoids.

The amount of non-phytocannabinoid containing component in the BDS may be less than 45%, through 40%, 35%, 30%, 25%, 20% to 15% or less of the total extract. The actual amount is likely to depend on the starting material used and the method of extraction used.

The "principle monoterpene/s" in a BDS is the monoterpene that is present in an amount that is higher than that of the other monoterpenes. Preferably the principle monoterpene/s is present in an amount greater than 20% (w/w) of the total terpene content. More preferably the principle monoterpene is present in an amount greater than 30% (w/w) of the total terpene content, more preferably still greater than 40% (w/w) of the total terpene content, and more preferably still greater than 50% (w/w) of the total terpene content. The principle monoterpene is preferably a myrcene or pinene. In some cases there may be two principle monoterpenes. Where this is the case the principle monoterpenes are preferably a pinene and/or a myrcene.

The "principle sesquiterpene" in a BDS is the sesquiterpene that is present in an amount that is higher than all the other sesquiterpenes. Preferably the principle sesquiterpene is present in an amount greater than 20% (w/w) of the total terpene content, more preferably still greater than 30% (w/w) of the total terpene content. The principle sesquiterpene is preferably a caryophyllene and/or a humulene.

The sesquiterpene components may have a "secondary sesquiterpene". The secondary sesquiterpene is preferably a pinene, which is preferably present at an amount greater than 5% (w/w) of the total terpene content, more preferably the secondary sesquiterpene is present at an amount greater than 10% (w/w) of the total terpene content.

The secondary sesquiterpene is preferably a humulene which is preferably present at an amount greater than 5% (w/w) of the total terpene content, more preferably the secondary sesquiterpene is present at an amount greater than 10% (w/w) of the total terpene content.

Alternatively botanical extracts may be prepared by introducing isolated phytocannabinoids or their synthetic equivalent into a non-cannabinoid plant fraction as can be obtained from a zero cannabinoid plant or one or more non-cannabinoid components found in the *cannabis* plant such as terpenes.

The structures of the phytocannabinoids CBDV, CBD, CBCV, CBC, THCV and THC are as shown below:

CBDV   Cannabidivarin

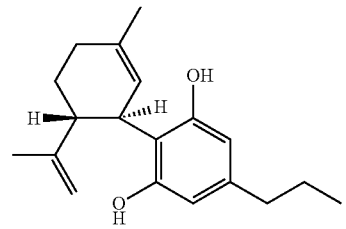 [SMILES: C=C(C)[C@@H]1CCC(C)=C[C@H]1c1c(O)cc(CCC)cc1O]

CBD   Cannabidiol

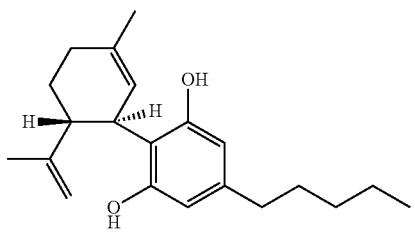 [SMILES: C=C(C)[C@@H]1CCC(C)=C[C@H]1c1c(O)cc(CCCCC)cc1O]

CBCV   Cannabichromene propyl variant

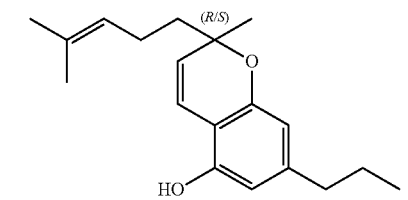 [SMILES: CCCc1cc(O)c2c(c1)OC(C)(CCC=C(C)C)C=C2]

CBC   Cannabichromene

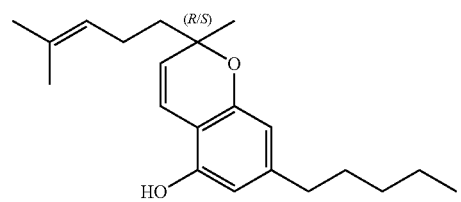 [SMILES: CCCCCc1cc(O)c2c(c1)OC(C)(CCC=C(C)C)C=C2]

THCV   Tetrahydrocannabivarin

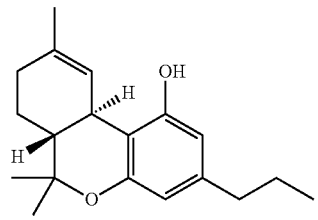 [SMILES: CCCc1cc(O)c2c(c1)OC(C)(C)[C@@H]1CCC(C)=C[C@@H]21]

| THC | Tetrahydrocannabinol | 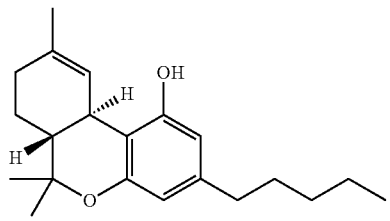 |

Phytocannabinoids can be found as either the neutral (decarboxylated form) or the carboxylic acid form depending on the method used to extract the cannabinoids. For example it is known that heating the carboxylic acid form will cause most of the carboxylic acid form to decarboxylate into the neutral form.

Where a synthetic phytocannabinoid is used the term is intended to include compounds, metabolites or derivatives thereof, and pharmaceutically acceptable salts of such compounds.

The term "pharmaceutically acceptable salts" refers to salts or esters prepared from pharmaceutically acceptable non-toxic bases or acids, including inorganic bases or acids and organic bases or acids, as would be well known to persons skilled in the art. Many suitable inorganic and organic bases are known in the art.

Phytocannabinoids can occur as either the pentyl (5 carbon atoms) or propyl (3 carbon atoms) variant. Initially it was thought that the propyl and pentyl variants would have similar properties, however recent research suggests this is not true. For example the phytocannabinoid THC is known to be a CB1 receptor agonist whereas the propyl variant THCV has been discovered to be a CB1 receptor antagonist meaning that it has almost opposite effects. This is confirmed by Pertwee (2000) in Cannabinoid receptor ligands: clinical and neuropharmacological considerations relevant to future drug discovery and development, It is an object of the present invention to identify compositions which are safe and efficacious for use in the treatment of neurological conditions, characterized by hyper-excitability of the central nervous system, convulsions or seizures such as occur in epilepsy.

Indeed, a major drawback with existing standard anti-epileptic drugs (SAEDs) is that 30% are refractory to existing treatments and there are also notable motor side effects in the existing therapies. Thus it is desirable to use compounds or combinations which reduce or are absent of such side effects.

BRIEF SUMMARY OF THE DISCLOSURE

In accordance with a first aspect of the present invention there is provided a composition comprising or consisting essentially of the phytocannabinoids cannabidivarin (CBDV) and cannabidiol (CBD).

Preferably the composition further comprising one or more excipients.

Preferably the composition further comprises at least one non-cannabinoid component of *cannabis*. More preferably the at least one non-cannabinoid component of *cannabis* is or comprises a terpene.

With reference to terpenes it should be noted that terpenes can be classified further into monoterpenes or sesquiterpenes. Common monoterpenes found in *cannabis* include myrcene and pinene and common sesquiterpenes found in *cannabis* include caryophyllenes and humulene.

Preferably the composition comprises or consists essentially of CBDV, CBD and one or more cannabichromene type compounds. More preferably the one or more cannabichromene type compounds is cannabichromene propyl variant (CBCV) and/or cannabichromene (CBC).

Preferably the composition is absent or substantially absent of any other cannabinoids. More preferably the composition is absent or substantially absent of the cannabinoids tetrahydrocannabivarin (THCV) and/or tetrahydrocannabinol (THC).

In particular the composition should comprise less than 0.3% (w/w) THC.

Preferably the composition comprises or consists essentially of the cannabinoids CBDV and CBD in a ratio of from 7:1 to 1:2 (CBDV:CBD). More preferably the CBDV and CBD are present in a ratio of from 5:1 to 1:1 (CBDV:CBD). More preferably still the CBDV and CBD are present in a ratio of 4.5:1 to 2:1 (CBDV:CBD).

Preferably the composition is packaged for delivery in a unit dosage form. More preferably the unit dosage form comprises from 500 to 2000 mg CBDV and from 100 to 600 mg CBD.

A "unit dose" is herein defined as a maximum dose of medication that can be taken at any one time or within a specified dosage period such as for example, 4 hours.

In a further embodiment of the present invention the composition further comprises a standard anti-epileptic drug (SAED).

A standard anti-epileptic drug is a medicament with anti-convulsant activity that is or has been used in the treatment of epilepsy.

In accordance with a second aspect of the present invention there is provided an extract or BDS comprising the phytocannabinoids CBDV and CBD but substantially absent of the cannabinoids THCV and THC.

The cannabinoids THCV and THC may not desirable components of a composition for use in the treatment of epilepsy for several reasons. In the case of THCV the fact that this phytocannabinoid is a known CB1 receptor antagonist gives rise to questions over the appropriateness of THCV for use in the treatment of epilepsy, particularly when one considers the evidence provided by Deshpande et al. that CB1 antagonists may be pro-convulsant and may give rise to suicidal tendencies. In the case of THC it is not clearly known whether THC is a pro- or anti-convulsant, however it is widely acknowledged that some of the side effects caused by THC, such as psychosis and anxiety, are particularly undesirable.

Preferably the extract or BDS further comprises one or more non-cannabinoid component(s).

In accordance with a third aspect of the present invention there is provided a combination of the phytocannabinoids cannabidivarin (CBDV) and cannabidiol (CBD) for use in the treatment of neurological conditions, characterised by hyper-excitability of the central nervous system, convulsions or seizures.

Preferably the combination of the neurological condition is epilepsy. More preferably the type of epilepsy to be treated is generalised seizure.

Preferably the combination of the phytocannabinoids cannabidivarin (CBDV) and cannabidiol (CBD) further comprises a standard anti-epileptic drug (SAED).

Preferably the combination of the phytocannabinoids CBDV and CBD are absent or substantially absent of any other cannabinoids. More preferably the composition is absent or substantially absent of the cannabinoids tetrahydrocannabivarin (THCV) and/or tetrahydrocannabinol (THC).

In accordance with a fourth aspect of the present invention there is provided the use of a combination of the phytocannabinoids cannabidivarin (CBDV) and cannabidiol (CBD) in the manufacture of a medicament for use in the treatment of neurological conditions, characterised by hyper-excitability of the central nervous system, convulsions or seizures.

Preferably the medicament is absent or substantially absent of any other cannabinoids. More preferably the composition is absent or substantially absent of the cannabinoids tetrahydrocannabivarin (THCV) and/or tetrahydrocannabinol (THC).

In accordance with a fifth aspect of the present invention there is provided a method for the treatment of neurological conditions, characterised by hyper-excitability of the central nervous system, convulsions or seizures, which comprises administering to a subject in need thereof a therapeutically effective amount of a combination of the phytocannabinoids cannabidivarin (CBDV) and cannabidiol (CBD).

Preferably the therapeutically effective amount of a combination of the phytocannabinoids cannabidivarin (CBDV) and cannabidiol (CBD) is absent or substantially absent of any other cannabinoids. More preferably the composition is absent or substantially absent of the cannabinoids tetrahydrocannabivarin (THCV) and/or tetrahydrocannabinol (THC).

BRIEF DESCRIPTION OF THE DRAWINGS

Embodiments of the invention are further described hereinafter with reference to the accompanying drawings, in which.

Figure 1:
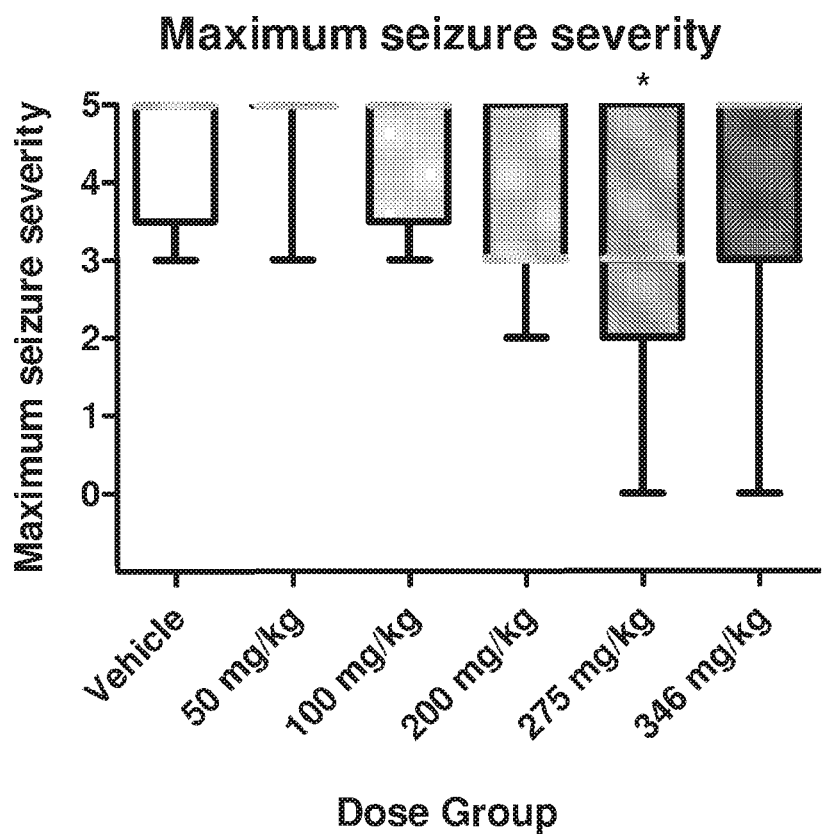
FIG. 1 shows the maximum seizure severity of the CBDV (-/-) BDS in the PTZ model of epilepsy.

The CBDV (-/-) BDS is used to designate a CBDV BDS from which THCV and THC have been selectively removed.

DETAILED DESCRIPTION

Example 1 below describes the use of a CBDV botanical drug substance (BDS) from which the cannabinoids THCV and THC have been selectively removed, hereinafter CBDV (-/-) BDS. The PTZ model of generalized seizures in epilepsy was used to determine the anti-convulsant activity of the test article.

Example 1

Use of a Composition Comprising CBDV and CBD in the PTZ Model of Generalised Seizures Methodology:

Animals:

Male Wistar rats (P24-29; 75-110g) were used to assess the combined effect of a composition comprising the phytocannabinoids CBDV and CBD in the PTZ model of generalised seizures. Animals were habituated to the test environment, cages, injection protocol and handling prior to experimentation. Animals were housed in a room at 21° C. on a 12 hour light: dark cycle (lights on 0900) in 50% humidity, with free access to food and water.

The human dose equivalent (HED) can be estimated using the following formula:

$$HED = \text{Animal dose (mg/kg) multiplied by } \frac{\text{Animal } K_m}{\text{Human } K_m}$$

The $K_m$ for a rat is 6 and the $K_m$ for a human is 37.

Thus, for a human of approx 60 Kg a 200 mg/Kg dose in rat would equate to a human daily dose of about 2000 mg.

Composition

A composition was prepared using a CBDV botanical drug substance (BDS) that had been further prepared by centrifugal partition chromatography to remove the cannabinoids THCV and THC, such that the cannabinoids consisted essentially of CBDV and CBD, and lesser amounts of CBCV and CBC. This BDS is termed CBDV (-/-) BDS for the purpose of this application.

Experimental Setup:

Five 6 L Perspex tanks with lids were placed on a single bench with dividers between them. Closed-circuit television (CCTV) cameras were mounted onto the dividers to observe rat behaviour. Sony Topica CCD cameras (Bluecherry, USA) were linked via BNC cables to a low-noise PC via Brooktree digital capture cards (Bluecherry, USA). Zoneminder (http://www.zoneminder.com) software was used to monitor rats, start and end recordings and manage video files. In-house Linux scripts were used to encode video files into a suitable format for further offline analysis using The Observer (Noldus Technologies).

PTZ Model:

A range of doses of PTZ (50-100 mg/kg body weight) were used to determine the best dose for induction of seizures. As a result, a dose of 85 mg/kg injected intraperitoneally (IP; stock solution 50 mg/ml in 0.9% saline) were used to screen the CBDV (-/-) BDS test article.

Experimental Protocols:

On the day of testing, the CBDV (-/-) BDS was administered via intra-peritoneal (i.p.) injection at doses of 50, 100, 200, 275 and 346 mg/kg alongside animals that were injected with a matched volume of the cannabinoid vehicle (2:1:17 ethanol:Cremophor:saline), which served as the negative control group, (giving defined doses of CBDV and CBD as set out in Table 1.1 below). Animals were then observed for 1 hour, after which time they received an IP injection of 85 mg/kg PTZ. Negative vehicle controls were performed in parallel with cannabinoid-dosed subjects. After receiving a dose of PTZ, animals were observed and videoed to determine the severity of seizure and latency to several seizure behaviour types (see in vivo analysis, below). Animals were filmed for half an hour after last sign of seizure, and then returned to their cage.

Dose Groups:

Table 1.1 below demonstrates the respective content of the cannabinoids CBDV and CBD in the different dose groups of the CBDV (−/−) BDS.

TABLE 1.1

| Dose group (amount of test article) | CBDV content (mg/kg) | CBD content (mg/kg) | Ratio (CBDV:CBD) |
|---|---|---|---|
| Vehicle | 0 | 0 | — |
| 50 mg/kg | 29 | 7 | 4.14:1 |
| 100 mg/kg | 58 | 14 | 4.14:1 |
| 200 mg/kg | 116 | 27 | 4.29:1 |
| 275 mg/kg | 159 | 38 | 4.18:1 |
| 346 mg/kg | 200 | 47 | 4.25:1 |

In Vivo Analysis:

Animals were observed during experimental procedures, but all analysis was performed offline on recorded video files using The Observer behavioural analysis software (Noldus, Netherlands). A seizure severity scoring system was used to determine the levels of seizure experienced by subjects (Pohl & Mares, 1987). All signs of seizure were detailed for all animals.

TABLE 1.2

Seizure severity scoring scale, adapted from Pohl & Mares, 1987.

| Seizure score | Behavioural expression | Righting reflex |
|---|---|---|
| 0 | No changes to behaviour | Preserved |
| 0.5 | Abnormal behaviour (sniffing, excessive washing, orientation) | Preserved |
| 1 | Isolated myoclonic jerks | Preserved |
| 2 | Atypical clonic seizure | Preserved |
| 3 | Fully developed bilateral forelimb clonus | Preserved |
| 3.5 | Forelimb clonus with tonic component and body twist | Preserved |
| 4 | Tonic-clonic seizure with suppressed tonic phase | Lost |
| 5 | Fully developed tonic-clonic seizure | Lost |
| 6 | Death | |

Latency from Injection of PTZ to Specific Indicators of Seizure Development:

The latency (in seconds) from injection of PTZ to first myoclonic jerk (FMJ; score of 1), and to the animal attaining "forelimb clonus with tonic component and body twist" (score of 3.5) were recorded. FMJ is an indicator of the onset of seizure activity, whilst >90% of animals developed scores of 3.5, and so is a good marker of the development of more severe seizures. Data are presented as the mean±S.E.M. within an experimental group.

Maximum Seizure Severity:

This is given as the median value for each experimental group based on the scoring scale below.

Percentage Mortality:

The percentage of animals within an experimental group that died as a result of PTZ-induced seizures. Note that the majority of animals that developed tonic-clonic seizures (scores of 4 and 5) died as a result, and that a score of 6 (death) automatically denotes that the animal also experienced tonic-clonic seizures.

Seizure Duration:

The time (in seconds) from the first sign of seizure (typically FMJ) to either the last sign of seizure or, in the case of subjects that died, the time of death—separated into animals that survived and those that did not. This is given as the mean±S.E.M. for each experimental group.

Statistics:

For measures of latency and severity, one way analysis of variance (ANOVA) was performed on all the groups together in order to detect overall effects of the test article ($p \leq 0.05$ considered significant), and is denoted by a '*' in the figures.

Significant ANOVA results were followed by post hoc tests to test differences between vehicle and drug groups (Tukey's test, $p \leq 0.05$ considered significant), and is denoted by a '*' in the figures.

Results:

FIG. 1 illustrates the maximum seizure severity, a significant effect of the CBDV (−/−) BDS on the maximum seizure severity was observed at a dose of 275 mg/kg CBDV (−/−) BDS.

Figure 2:
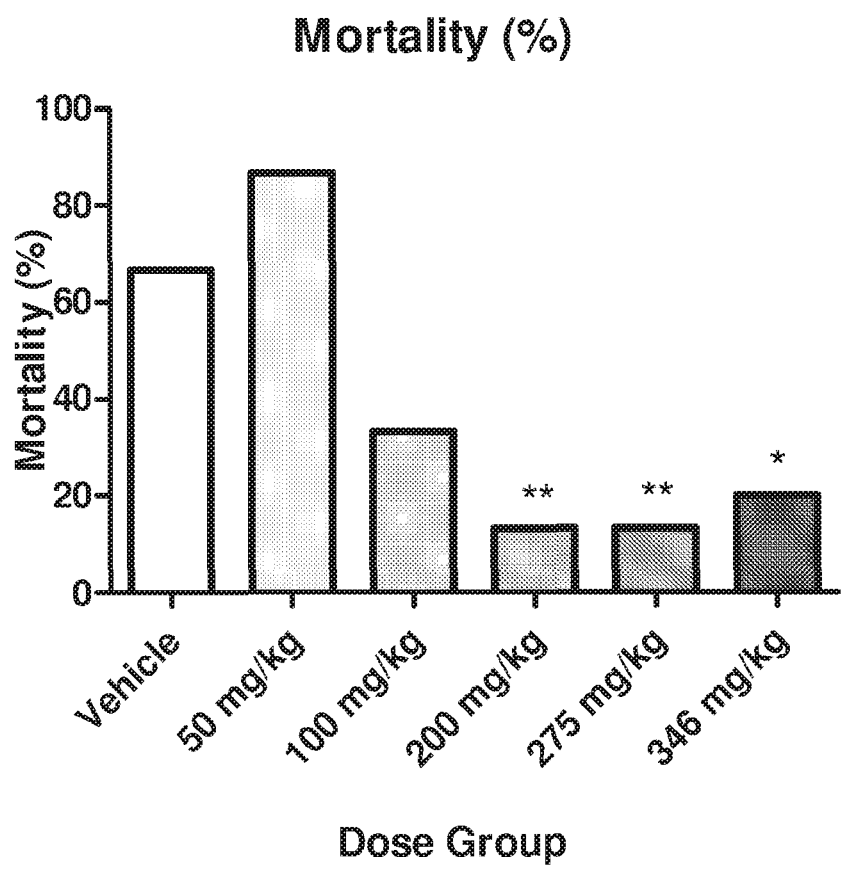
FIG. 2 shows the percentage mortality of the CBDV (-/-) BDS in the PTZ model of epilepsy.

FIG. 2 illustrates the percentage mortality of the animals dosed with the CBDV (−/−) BDS. As can be observed the animals given the, 200 and 275 mg/kg CBDV (−/−) BDS had a strongly statistical significance and the animals given the highest dose (346 mg/kg CBDV (−/−) BDS had a less statistical significance but still resulted in a decrease in the percentage mortality.

Figure 3:
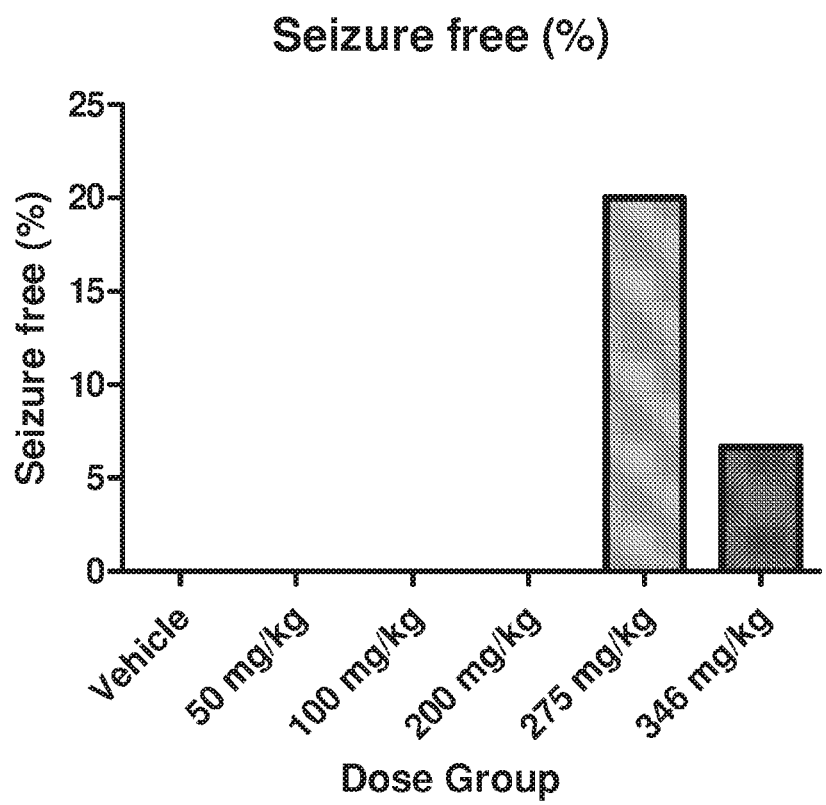
FIG. 3 shows the percentage of animals that were seizure free in the CBDV (-/-) BDS in the PTZ model of epilepsy.

FIG. 3 illustrates that although no significant effect of the CBDV (−/−) BDS was observed on the percentage of animals that were seizure free, the 275 mg/kg dose resulted in 20% of the animals becoming seizure free.

Figure 4:
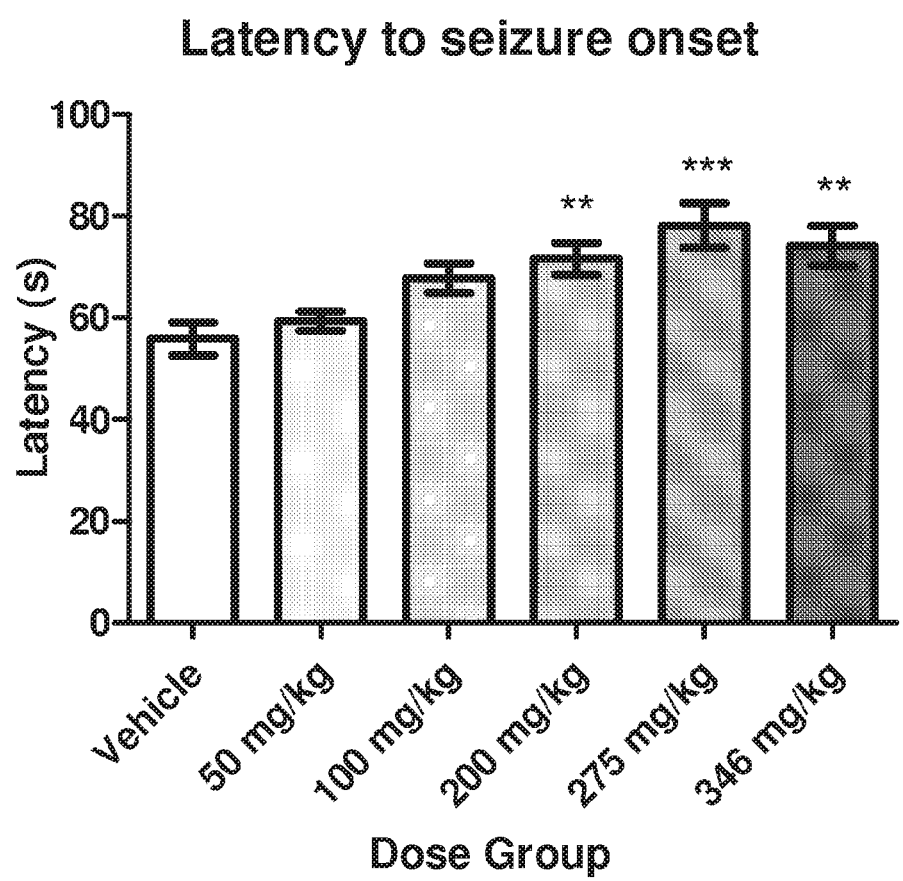
FIG. 4 shows the latency to seizure onset in the CBDV (-/-) BDS in the PTZ model of epilepsy.

FIG. 4 illustrates the latency to seizure onset was statistically increased in all of the high dose groups (200, 275 and 346 mg/kg) of the CBDV (−/−) BDS.

Figure 5:
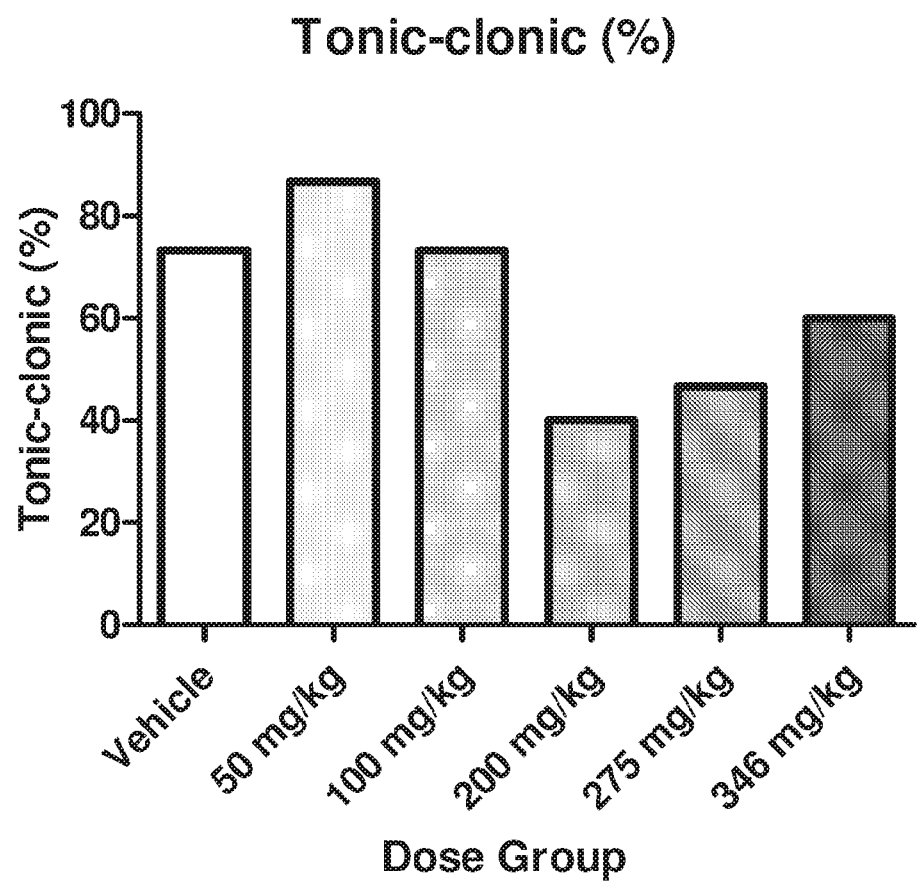
FIG. 5 shows the percentage of animals that experienced tonic-clonic seizures in the CBDV (-/-) BDS in the PTZ model of epilepsy.

FIG. 5 illustrates the percentage of animals that experienced the severe tonic-clonic seizures decreased in the higher dose groups (200, 275 and 346 mg/kg) of the CBDV (−/−) BDS; however the decrease was not statistically significant.

Conclusion:

From the above data it would appear that the CBDV (−/−) BDS composition will reduce seizure severity and mortality and increase latency to onset of seizures, making it a desirable composition for use in the treatment of epilepsy.

The omission of the cannabinoids THCV and THC from a BDS further obviates concerns associated with CB1 antagonism and psychosis.

Example 2

Analysis of CBDV (−/−) BDS

The CBDV (−/−) BDS which was used in Example 1 above can be obtained using centrifugal partition chromatography (CPC) of a CBDV (+/+) BDS.

A CBDV (−/−) BDS has been produced and analysed as described in Table 2.1 below:

TABLE 2.1

| CBDV (−/−) BDS amount in total and range | | | |
|---|---|---|---|
| CBDV (−/−) BDS | Amount (% w/w) | Range (±10%) | Range (±25%) | Range (±50%) |
| CBDVA | 0.14 | 0.13-0.15 | 0.11-0.18 | 0.07-0.21 |
| CBDV | 41.19 | 37.07-45.31 | 30.89-51.49 | 20.60-61.79 |
| CBDA | 0.07 | 0.06-0.08 | 0.05-0.09 | 0.04-0.11 |
| CBG | 0.59 | 0.53-0.65 | 0.44-0.74 | 0.30-0.89 |

TABLE 2.1-continued

CBDV (−/−) BDS amount in total and range

| CBDV (−/−) BDS | Amount (% w/w) | Range (±10%) | Range (±25%) | Range (±50%) |
|---|---|---|---|---|
| CBD | 17.70 | 15.93-19.47 | 13.28-22.13 | 8.85-26.55 |
| CBCV | 4.35 | 3.92-4.79 | 3.26-5.44 | 2.18-6.53 |
| CBDV (related substances) | 2.20 | 1.98-2.42 | 1.65-2.75 | 1.10-3.30 |
| CBC | 0.93 | 0.84-1.02 | 0.70-1.16 | 0.47-1.40 |
| Total Cannabinoids | 67.17 | | | |
| Total Non-cannabinoids | 32.83 | | | |

The total phytocannabinoid containing fraction of CBDV (−/−) BDS comprises approximately 41% of the total BDS. According to variation this fraction may vary by ±10% up to ±50%.

TABLE 2.2

Cannabidivarin (−/−) BDS by percentage cannabinoid

| CBDV (−/−) BDS | Amount (% of total cannabinoid) |
|---|---|
| CBDVA | 0.23 |
| CBDV | 61.30 |
| CBDA | 0.11 |
| CBG | 0.96 |
| CBD | 28.90 |
| CBCV | 7.11 |
| CBDV (related substances) | 3.60 |
| CBC | 1.52 |

The amount of the principle phytocannabinoid in the CBDV (−/−) BDS as a percentage of the phytocannabinoid containing fraction is approximately 61%. According to variation this fraction may vary by ±10% up to ±50%.

In this Example it is intended that references be made to the principle or secondary components independently of the 'other' cannabinoids.

Comparative Example 3

CBDV (+१+) BDS Analysis

The following example is included to provide details of the components of the CBDV (+/+) BDS. The CBDV (+/+) BDS was obtained by subcritical $CO_2$ extraction. It comprises, as well as CBDV, the cannabinoids CBD, THCV and THC in significant quantities (each greater than 1% by weight as a percentage of total cannabinoid content). THC has been ascribed a pro-convulsant and it can also have marked psychoactive effects in addition to other side effects such as anxiety which are not desired. THCV whilst showing anti-convulsant activity specific to generalized seizures in epilepsy is a CB1 antagonist and following evidence to suggest that the CB1 antagonist rimonabant may cause epilepsy and other undesired effects it may be desirable to remove these cannabinoids from a BDS whilst still retaining the non-cannabinoid component(s) which may contribute to the activity of the BDS.

A CBDV (+१+) BDS can be obtained from extraction of CBDV-rich plants. Such chemovars are bred specifically to produce a significant proportion of their cannabinoids as CBDV.

The CBDV chemotype results from the breeding of plants which carry both postulated $B_D$ and $A_{PR}$ genes.

The $B_D$ gene instruct the plants to synthesize the cyclic part of the CBD molecule and the $A_{PR}$ gene instructs the plant to synthesize this molecule with a propyl side chain, as opposed to the usual pentyl chain found in CBD.

A CBDV chemovar has been bred and the BDS analysed as described in Table 3.1 below:

TABLE 3.1

CBDV (+/+) BDS amount in total and range

| CBDV (+/+) BDS | Amount (% w/w) | Range (± 10%) | Range (± 25%) | Range (± 50%) |
|---|---|---|---|---|
| CBDVA | 0.14 | 0.13-0.15 | 0.11-0.18 | 0.07-0.21 |
| CBDV | 41.19 | 37.07-45.31 | 30.89-51.49 | 20.60-61.79 |
| CBDA | 0.07 | 0.06-0.08 | 0.05-0.09 | 0.04-0.11 |
| CBG | 0.59 | 0.53-0.65 | 0.44-0.74 | 0.30-0.89 |
| CBD | 17.70 | 15.93-19.47 | 13.28-22.13 | 8.85-26.55 |
| THCV | 3.06 | 2.75-6.12 | 2.30-3.83 | 1.53-4.59 |
| CBCV | 4.35 | 3.92-4.79 | 3.26-5.44 | 2.18-6.53 |
| THC | 0.88 | 0.79-0.97 | 0.66-1.10 | 0.44-1.32 |
| CBDV (related substances) | 2.20 | 1.98-2.42 | 1.65-2.75 | 1.10-3.30 |
| CBC | 0.93 | 0.84-1.02 | 0.70-1.16 | 0.47-1.40 |
| Total Cannabinoids | 71.11 | | | |
| Total Non-cannabinoids | 28.89 | | | |

The total phytocannabinoid containing fraction of CBDV (+/+) BDS comprises approximately 41% of the total BDS. According to variation this fraction may vary by ±10% up to ±50%.

TABLE 3.2

CBDV (+/+) BDS by percentage cannabinoid

| CBDV (+/+) BDS | Amount (% of total cannabinoid) |
|---|---|
| CBDVA | 0.20 |
| CBDV | 57.92 |
| CBDA | 0.10 |
| CBG | 0.83 |
| CBD | 24.89 |
| THCV | 4.30 |
| CBCV | 6.12 |
| THC | 1.24 |
| CBDV (related substances) | 3.09 |
| CBC | 1.31 |

The amount of the principle phytocannabinoid in the CBDV (+/+) BDS as a percentage of the phytocannabinoid containing fraction is approximately 58%. According to variation this fraction may vary by ±10% up to ±50%.

In this Example it is intended that references be made to the principle or secondary components independently of the 'other' cannabinoids.

Comparative Example 4

Non-Cannabinoid Profile of a High Phytocannabinoid Containing Plant

This comparative Example is included to demonstrate a typical terpene profile obtained from a *cannabis* plant that has been bred to produce a high quantity of cannabinoids.

The non-cannabinoid components of a phytocannabinoid BDS may play an important role in the BDS's pharmacology. As such the terpene profile is classified below. The following tables illustrate the terpene profile of a CBD chemovar which is representative of a high phytocannabinoid containing plant. Five plants were freshly harvested and extracted using steam distillation. The principle monoterpene and sesquiterpene are highlighted in bold.

TABLE 4.1

Monoterpene amount by percentage of total terpene fraction and ranges

| Monoterpenes | Amount (% of terpene fraction) | Range (±10%) | Range (±25%) | Range (±50%) |
|---|---|---|---|---|
| Pinene (alpha & beta) | 10.56 | 9.50-11.62 | 7.92-13.20 | 5.28-15.84 |
| Myrcene | 39.46 | 35.51-43.41 | 29.60-49.33 | 19.73-59.19 |
| Limonene | 4.14 | 3.73-4.55 | 3.11-5.18 | 2.07-6.21 |
| Beta-ocimene | 4.04 | 3.64-4.44 | 3.03-5.05 | 2.02-6.06 |
| Total | 58.20 | | | |

The monoterpene containing fraction comprises approximately 52-64% (w/w) of the total terpene fraction.

TABLE 4.2

Monoterpene amount by percentage of monoterpenes

| Monoterpenes | Amount (% of monoterpene fraction) |
|---|---|
| Pinene (alpha & beta) | 18.14 |
| Myrcene | 67.80 |
| Limonene | 7.12 |
| Beta-ocimene | 6.94 |

The amount of the principle monoterpene myrcene in the monoterpene fraction as a percentage of the monoterpene fraction is approximately 61-75% (w/w). The monoterpene fraction also has a secondary monoterpene pinene which is present at approximately 16.3-20% (w/w) of the monoterpene fraction.

TABLE 4.3

Sesquiterpene amount by percentage of total terpene fraction and ranges

| Sesquiterpenes | Amount (% of terpene fraction) | Range (±10%) | Range (±25%) | Range (±50%) |
|---|---|---|---|---|
| Caryophyllenes (t & oxide) | 29.27 | 26.34-32.20 | 21.95-36.59 | 14.64-43.91 |
| Bergotamene | 0.18 | 0.16-0.20 | 0.14-0.23 | 0.09-0.27 |
| Humulene | 7.97 | 7.17-8.77 | 5.98-9.96 | 3.99-11.96 |
| Aromadendrene | 0.33 | 0.30-0.36 | 0.25-0.41 | 0.17-0.50 |
| Selinene | 0.59 | 0.53-0.65 | 0.44-0.74 | 0.30-0.89 |
| Anon | 0.44 | 0.40-0.48 | 0.33-0.55 | 0.22-0.66 |
| Farnesene (Z, E & alpha) | 1.55 | 1.40-1.71 | 1.16-1.94 | 0.78-2.33 |
| alpha Gurjunene | 0.12 | 0.11-0.13 | 0.09-0.15 | 0.06-0.18 |
| Bisabolene | 0.39 | 0.35-0.43 | 0.29-0.49 | 0.20-0.59 |
| Nerolidol | 0.43 | 0.39-0.47 | 0.32-0.54 | 0.22-0.65 |
| Diepicedrene-1-oxide | 0.38 | 0.34-0.42 | 0.29-0.48 | 0.19-0.57 |
| Alpha-Bisabolol | 0.16 | 0.14-0.18 | 0.12-0.20 | 0.08-0.24 |
| Total | 41.80 | | | |

The sesquiterpene containing fraction comprises approximately 27-32% (w/w) of the total terpene fraction.

TABLE 4.4

Sesquiterpene amount by percentage of sesquiterpenes

| Sesquiterpenes | Amount (% of sesquiterpene fraction) |
|---|---|
| Caryophyllenes (t & oxide) | 70.02 |
| Bergotamene | 0.43 |
| Humulene | 19.07 |
| Aromadendrene | 0.79 |
| Selinene | 1.41 |
| Anon | 1.05 |
| Farnesene (Z, E & alpha) | 3.71 |
| alpha Gurjunene | 0.29 |
| Bisabolene | 0.93 |
| Nerolidol | 1.03 |
| Diepicedrene-1-oxide | 0.91 |
| Alpha-Bisabolol | 0.38 |

Comparative Example 5

Non-Cannabinoid Profile of a 'Zero Cannabinoid' Plant

This comparative Example describes the terpene profile of a different *cannabis* plant to that described on Example 4 above and is reproduced here for comparative purposes.

Patent application number PCT/GB2008/001837 describes the production of a 'zero cannabinoid' plant. These plants were produced by selective breeding to produce a *Cannabis sativa* L plant that contained a generally qualitatively similar terpene profile as a *Cannabis sativa* L plant that produced cannabinoids yet it was devoid of any cannabinoids. These plants can be used to produce cannabinoid-free plant extracts which are useful control plants in experiments and clinical trials. A breakdown of the terpene profile produced in the plants can be found in the table below. The primary monoterpenes and sesquiterpene are highlighted in bold.

TABLE 5.1

Monoterpene amount by percentage of total terpene fraction and ranges

| Monoterpenes | Amount (% of terpene fraction) | Range (±10%) | Range (±25%) | Range (±50%) |
|---|---|---|---|---|
| Pinene (alpha & beta) | 29.34 | 26.41-32.27 | 22.01-36.68 | 14.67-44.01 |
| Myrcene | 29.26 | 26.33-32.19 | 21.95-36.58 | 14.63-43.89 |
| Limonene | 5.32 | 4.79-5.85 | 3.99-6.65 | 2.66-7.98 |
| Linalol | 4.50 | 4.05-4.95 | 3.38-5.63 | 2.25-6.75 |
| Verbenol (cis & trans) | 3.45 | 3.11-3.80 | 2.59-4.31 | 1.73-5.18 |
| Total | 71.87 | | | |

The monoterpene containing fraction comprises approximately 65-79% (w/w) of the total terpene fraction.

TABLE 5.2

Monoterpene amount by percentage of monoterpenes

| Monoterpenes | Amount (% of monoterpene fraction) |
|---|---|
| Pinene (alpha & beta) | 40.82 |
| Myrcene | 40.71 |
| Limonene | 7.41 |
| Linalol | 6.26 |

TABLE 5.3

Sesquiterpene amount by percentage of total terpene fraction and ranges

| Sesquiterpenes | Amount (% of terpene fraction) | Range (±10%) | Range (±25%) | Range (±50%) |
|---|---|---|---|---|
| Caryophyllenes (t & oxide) | 10.89 | 9.80-11.98 | 8.17-13.61 | 5.45-16.34 |
| Bergotamene | 2.51 | 2.26-2.76 | 1.88-3.14 | 1.26-3.77 |
| Farnesene (Z, E & alpha) | 3.43 | 3.09-3.77 | 2.57-4.29 | 1.72-5.15 |
| Humulene (& epoxide II) | 5.04 | 4.54-5.54 | 3.78-6.30 | 2.52-7.56 |
| delta guaiene | 2.40 | 2.16-2.64 | 1.80-3.00 | 1.20-3.60 |
| Bisabolene | 3.85 | 3.47-4.24 | 2.89-4.81 | 1.93-5.78 |
| Total | 28.12 | | | |

The sesquiterpene containing fraction comprises approximately 25-31% (w/w) of the total terpene fraction.

TABLE 5.4

Sesquiterpene amount by percentage of sesquiterpenes

| Sesquiterpenes | Amount (% of sesquiterpene fraction) |
|---|---|
| Caryophyllenes (t & oxide) | 38.73 |
| Bergotamene | 8.93 |
| Farnesene (Z, E & alpha) | 12.20 |
| Humulene (& epoxide II) | 17.92 |
| delta guaiene | 8.53 |
| Bisabolene | 13.69 |

The amount of the principle sesquiterpene caryophylene in the sesquiterpene fraction as a percentage of the sesquiterpene fraction is approximately 35-43% (w/w). The sesquiterpene fraction also has a secondary sesquiterpene humulene which is present at approximately 16-20% (w/w) of the sesquiterpene fraction.

Comparative Example 6

Use of CBDV (+/+) BDS in the PTZ Model of Generalised Seizures

This comparative Example was previously presented in GB1005364.3 (unpublished) patent application and is included here for representative purposes.

Methodology as described in Example 1.

CBDV (+/+) BDS was administered at four doses that yielded a dose of CBDV of 50 and 100 mg/kg. Table 6.1 below details the data obtained.

TABLE 5.1

| CBDV (+/+) BDS (mg/kg) | Mortality (%) |
|---|---|
| 0 | 26.3 |
| 50 | 16.7 |
| 100 | 0 |

As can be seen the CBDV (+/+) BDS exhibited a trend to decrease seizure-related mortality.

REFERENCES

ALGER, B. E. (2006) Not too excited? Thank your endocannabinoids. *Neuron*, 51, 393-5.

AMES FR. (1986) Anticonvulsant effect of cannabidiol. *South African Medical Journal* 69:14.

AVOLI, M., LOUVEL, J., PUMAIN, R. & KOHLING, R. (2005) Cellular and molecular mechanisms of epilepsy in the human brain. *Prog Neurobiol*.

BOSTANCI, M. O. & BAGIRICI, F. (2006) The effects of octanol on penicillin induced epileptiform activity in rats: an in vivo study. *Epilepsy Res*, 71, 188-94.

BRUST, J. C., NG, S. K., HAUSER, A. W. & SUSSER, M. (1992) Marijuana use and the risk of new onset seizures. *Trans Am Clin Climatol Assoc*, 103, 176-81.

CONSROE, P. F., WOOD, G. C. & BUCHSBAUM, H. (1975) Anticonvulsant Nature of Marihuana Smoking. *J. American Medical Association* 234 306-307

CUNHA, J. M., CARLINI, E. A., PEREIRA, A. E., RAMOS, 0. L., PIMENTEL, C., GAGLIARDI, R., SANVITO, W. L., LANDER, N. & MECHOULAM, R. (1980) Chronic administration of cannabidiol to healthy volunteers and epileptic patients. *Pharmacology*, 21, 175-85.

DAVIS, M. I., RONESI, J. & LOVINGER, D. M. (2003) A Predominant Role for Inhibition of the Adenylate Cyclase/Protein Kinase A Pathway in ERK Activation by Cannabinoid Receptor 1 in N1E-115 Neuroblastoma Cells. *J. Biol. Chem.*, 278, 48973-48980.

DREIFUSS, F. E., BANCAUD, J., HENRIKSEN, O., RUBIO-DONNADIEU, F. PENRY, J. K. & SEINO, M. (1981) Proposal for revised clinical and electroencephalographic classification of epileptic seizures. *Epilepsia*, 22, 489-501.

FERDINAND, R. F., VAN DER ENDE, J., BONGERS, I., SELTEN, J. P., HUIZINK, A. & VERHULST, F. C. (2005) *Cannabis*—psychosis pathway independent of other types of psychopathology. *Schizophr Res*, 79, 289-95.

FISHER, R. S., VICKREY, B. G., GIBSON, P., HERMANN, B., PENOVICH, P., SCHERER, A. & WALKER, S. (2000) The impact of epilepsy from the patient's perspective I. Descriptions and subjective perceptions. *Epilepsy Res*, 41, 39-51.

GASTAUT, H. (1970) Clinical and Electroencephalographical Classification of Epileptic Seizures. *Epilepsia*, 11, 102-112.

LUTZ, B. (2004) On-demand activation of the endocannabinoid system in the control of neuronal excitability and epileptiform seizures. *Biochem Pharmacol*, 68, 1691-8.

MACKIE, K. (2006) Cannabinoid receptors as therapeutic targets. *Annu Rev Pharmacol Toxicol*, 46, 101-22.

MCCORMICK, D. A. & CONTRERAS, D. (2001) On the cellular and network bases of epileptic seizures. *Annu Rev Physiol*, 63, 815-46.

MERLIS, J. K. (1970) Proposal for an International Classification of the Epilepsies. *Epilepsia*, 11, 114-119.

N G et al. (1990) Illicit drug use and the risk of new-onset seizures, *American Journal of Epidemiology* 132: 47-57.

OBAY, B. D., TASDEMIR, E., TUMER, C., BILGIN, H. M. & SERMET, A. (2007) Antiepileptic effects of ghrelin on pentylenetetrazole-induced seizures in rats. *Peptides,* 28, 1214-9.

PEREIRA, M. B., FREITAS, R. L., ASSIS, M. A., SILVA, R. F., FONTELES, M. M., FREITAS, R. M. & TAKAHASHI, R. N. (2007) Study pharmacologic of the GABAergic and glutamatergic drugs on seizures and status epilepticus induced by pilocarpine in adult Wistar rats. *Neurosci Lett,* 419, 253-7.

PERTWEE R. G., (2000) Cannabinoid receptor ligands: clinical and neuropharmacological considerations, relevant to future drug discovery and development. *Exp. Opin. Invest. Drugs* 9(7):

RAUCA, C., WISWEDEL, I., ZERBE, R., KEILHOFF, G. & KRUG, M. (2004) The role of superoxide dismutase and alpha-tocopherol in the development of seizures and kindling induced by pentylenetetrazol—influence of the radical scavenger alpha-phenyl-N-tert-butyl nitrone. *Brain Res,* 1009, 203-12.

SANDER, J. W. (2003) The epidemiology of epilepsy revisited. *Curr Opin Neurol,* 16, 165-70.

SWANN, J. W. (2004) The effects of seizures on the connectivity and circuitry of the developing brain. *Ment Retard Dev Disabil Res Rev,* 10, 96-100.

TREMBLY B. SHERMAN M. (1990) Double-blind clinical study of cannabidiol as a secondary anticonvulsant. Marijuana '90 *International Conference on Cannabis and Cannabinoids*. Kolympari, Crete, Jul. 8-11, 1990.

WINGERCHUK, D. (2004) *Cannabis* for medical purposes: cultivating science, weeding out the fiction. *Lancet,* 364, 315-6.

The invention claimed is:

1. A composition comprising or consisting essentially of cannabidivarin (CBDV) and cannabidiol (CBD), wherein the CBDV and CBD are present in a ratio of from 5:1 to 1:1 (CBDV:CBD).

2. The composition as claimed in claim 1, further comprising one or more excipients.

3. The composition as claimed in claim 1, further comprising at least one non-cannabinoid component of *cannabis*.

4. The composition as claimed in claim 3, wherein at least one non-cannabinoid component of *cannabis* comprises a terpene.

5. The composition as claimed in claim 1, wherein the composition further comprises, or consists essentially of CBDV, CBD and one or more cannabichromene type compounds.

6. The composition as claimed in claim 5, wherein the one or more cannabichromene type compounds is cannabichromene propyl variant (CBCV) and/or cannabichromene (CBC).

7. The composition as claimed in claim 1, which is absent or substantially absent of any other cannabinoids.

8. The composition as claimed in claim 7, wherein the any other cannabinoids are tetrahydrocannabivarin (THCV) and/or tetrahydrocannabinol (THC).

9. The composition as claimed in claim 1, wherein the CBDV and CBD are present in a ratio of 4.5:1 to 2:1 (CBDV:CBD).

10. The composition as claimed in claim 1, wherein a unit dosage form of the composition comprises from 500 to 2000 mg CBDV.

11. The composition as claimed in claim 1, wherein a unit dosage form of the composition comprises from 100 to 600 mg CBD.

12. The composition as claimed in claim 1, wherein the composition is an extract or botanical drug substance (BDS), and wherein the composition is substantially absent of tetrahydrocannabivarin (THCV) and tetrahydrocannabinol (THC).

13. A composition as claimed in claim 12, wherein the composition further comprises one or more non-cannabinoid component(s).

14. The combination, comprising:
a composition as claimed in claim 1, and
a standard anti-epileptic drug (SAED),
wherein the combination is configured for use in the treatment of neurological conditions that involve hyper-excitability of the central nervous system, convulsions or seizures.

15. The combination as claimed in claim 14, wherein the neurological condition is epilepsy.

16. The combination as claimed in claim 15, wherein the type of epilepsy to be treated is generalised seizure.

17. A method, comprising using a composition as claimed in claim 1 in the manufacture of a medicament for use in the treatment of neurological conditions that involve hyper-excitability of the central nervous system, convulsions or seizures.

18. A method for treating a neurological condition that involves hyper-excitability of the central nervous system, convulsions or seizures in a subject in need thereof, comprising administering to the subject a therapeutically effective amount of a composition as claimed in claim 1.

19. The method as claimed in claim 18, wherein the neurological condition is epilepsy.

20. The method as claimed in claim 19, wherein the type of epilepsy is generalised seizure.

21. The method as claimed in claim 18, wherein the composition further comprises at least one non-cannabinoid component of *cannabis.*

22. The method as claimed in claim 21, wherein at least one non-cannabinoid component of *cannabis* comprises a terpene.

23. The method as claimed in claim 18, wherein the composition further comprises one or more cannabichromene type compounds.

24. The method as claimed in claim 18, wherein the composition further comprises cannabichromene propyl variant (CBCV) and/or cannabichromene (CBC).

25. The method as claimed in claim 18, wherein the composition is absent or substantially absent of any other cannabinoids.

26. The method as claimed in claim 18, wherein the composition is absent or substantially absent of tetrahydrocannabivarin (THCV) and/or tetrahydrocannabinol (THC).

27. The method as claimed in claim 18, wherein the CBDV and CBD are present in the composition in a ratio of 4.5:1 to 2:1 (CBDV:CBD).

28. The method as claimed in claim 18, wherein a unit dosage form of the composition comprises from 500 to 2000 mg CBDV.

29. The method as claimed in claim 18, wherein a unit dosage form of the composition comprises from 100 to 600 mg CBD.

30. The method as claimed in claim 18, wherein a unit dosage form of the composition comprises: (i) from 100 to 600 mg CBD and (ii) from 500 to 2000 mg CBDV.

31. The method as claimed in claim 18, further comprising administering to the subject a standard anti-epileptic drug (SAED).

32. The composition as claimed in claim 1, wherein a unit dosage form of the composition comprises: (i) from 100 to 600 mg CBD and (ii) from 500 to 2000 mg CBDV.

33. The composition as claimed in claim 1, wherein the composition consists essentially of cannabidivarin (CBDV) and cannabidiol (CBD), and wherein the CBDV and CBD are present in a ratio of from 5:1 to 1:1 (CBDV:CBD).

34. The composition as claimed in claim 1, wherein the composition comprises:
cannabidivarin (CBDV) and cannabidiol (CBD), wherein the CBDV and CBD are present in a ratio of from 5:1 to 1:1 (CBDV:CBD);
one or more cannabichromene type compounds;
at least one non-cannabinoid component of *cannabis*; and
one or more excipients, wherein the composition is absent or substantially absent of any other cannabinoids.

35. The method for treating a neurological condition that involves hyper-excitability of the central nervous system, convulsions or seizures in a subject in need thereof, comprising administering to the subject a therapeutically effective amount of a composition as claimed in claim 33.

36. The method as claimed in claim 35, wherein the neurological condition is epilepsy.

37. The method as claimed in claim 36, wherein the type of epilepsy is generalised seizure.

38. The method as claimed in claim 35, further comprising administering to the subject a standard anti-epileptic drug (SAED).

39. The method for treating a neurological condition that involves hyper-excitability of the central nervous system, convulsions or seizures in a subject in need thereof, comprising administering to the subject a therapeutically effective amount of a composition as claimed in claim 34.

40. The method as claimed in claim 39, wherein the neurological condition is epilepsy.

41. The method as claimed in claim 40, wherein the type of epilepsy is generalised seizure.

42. The method as claimed in claim 39, further comprising administering to the subject a standard anti-epileptic drug (SAED).

* * * * *